US006825011B1

(12) United States Patent
Romantchikov

(10) Patent No.: US 6,825,011 B1
(45) Date of Patent: Nov. 30, 2004

(54) METHODS FOR INSERTION OF NUCLEIC ACIDS INTO CIRCULAR VECTORS

(75) Inventor: Yuri Romantchikov, Somerset, NJ (US)

(73) Assignee: Yuri Rumantichikov, Germantown, MD (US)

( * ) Notice: Subject to any disclaimer, the term of this patent is extended or adjusted under 35 U.S.C. 154(b) by 0 days.

(21) Appl. No.: 09/213,834

(22) Filed: Dec. 17, 1998

(51) Int. Cl.[7] .............................. C12N 15/66; C12N 9/90

(52) U.S. Cl. ............................. 435/91.41; 435/91.52; 435/320.1; 536/24.2

(58) Field of Search ...................... 435/91.41, 91.52, 435/233, 320.1, 69.1, 91.1, 91.21, 91.3, 91.4, 172.1, 172.3, 252.3, 254.2, 18; 536/24.2; 530/300, 350

(56) References Cited

U.S. PATENT DOCUMENTS 5,844,084 A * 12/1998 Guegler et al. ............. 530/351

FOREIGN PATENT DOCUMENTS

| WO | WO 98/38296 | 9/1998 |
|----|----|----|
| WO | WO 98/38297 | 9/1998 |
| WO | WO 98/38298 | 9/1998 |
| WO | WO 98/38299 | 9/1998 |

OTHER PUBLICATIONS

Debabov, V. G. Cloning of genes of bacteria on plasmids. Mol. Osn. Genet. Protsessov, Tr. Mezhdunar. Genet. Kongr., 14th (1981), pp. 234–239.*
Upton et al. Rapid and efficient method for cloning of blunt–ended DNA fragments. Gene. (1987), vol. 51 (1), pp. 69–75.*
Shizuya H et al, "Cloning and stable maintenance of 300–kilobase–pair fragments of human DNA in Escherichia coli using an F–factor–based vector", Proc Natl Acad Sci, vol. 89, Sep. 1992, pp. 8794–8797).*
Miki, T et al, "An efficient directional cloning system to construct cDNA libraries containing full–length inserts at high frequency", Gene, 83(1989), pp. 137–146.*
Aslanidis, C et al, "Minimal length requirment of the single–stranded tails for ligation–oindependent cloning (LIC) of PCR products", PCR Methods and Applications, Dec. 1994, vol. 4, No. 3, pp. 172–177.*
Fujimaki K et al, "DNA topoisomerase II inhibitos enhance random integration of transfected vectors into human chromosomes", Somatic Cell and Molecular Genetics, Jul. 1996, 22(4), pp. 279–290.*
Maniatis, T et al, "Molecular Cloning, A Laboratory Manual", Cold Spring Harbor Laboratory, 1982, pp 17–20.*
Aslanidis C, et al. Ligation–independent cloning of PCR products (LIC–PCR). Nucleic Acids Res. Oct. 25, 1990;18(20):6069–6074.

Bercovich JA, et al. Effect of DNA concentration on recombinant plasmid recovery after blunt–end ligation Biotechniques. Feb. 1992;12(2):190, 192–193.
Boyd AC. Turbo cloning: a fast, efficient method for cloning PCR products and other blunt–ended DNA fragments into plasmids. Nucleic Acids Res. Feb. 25, 1993;21(4):817–821.
Damak S, et al. A simple two–step method for efficient blunt–end ligation of DNA fragments. Biotechniques. Sep. 1993;15(3):448–450, 452.
Mead DA, et al. A universal method for the direct cloning of PCR amplified nucleic acid. Biotechnology (N Y). Jul. 1991;9(7):657–663.
Nisson PE, et al. Rapid and efficient cloning of Alu–PCR products using uracil DNA glycosyalse. PCR Methods Appl. Nov. 1991;1(2):120–123.
Pecenka V, et al. Simple and efficient method for cloning of large DNA fragments with identical ends into plasmid vectors. Nucleic Acid Res. May 11, 1988;16(9):4179.
Rashtchian A, et al. Uracil DNA glycosylase–mediated cloning of polymerase chain reaction–amplified DNA: application to genomic and cDNA cloning. Anal Biochem. Oct. 1992;206(1):91–97.
Revie D, et al. Kinetic analysis for optimization of DNA ligation reactions. Nucleic Acids Res. Nov. 11, 1988;16(21):10301–10321.
Sekiguchi J, et al. Covalent DNA binding by vaccinia topoisomerase results in unpairing of the thymine base 5'of the scissile bond. J Biol Chem Aug. 9, 1996;271(32):19436–19442.
Sekiguchi J, et al. Identification of contacts between topoisomerase I and its target DNA by site–specific photo-crosslinking. EMBO J. Jul. 1, 1996;15(13):3448–3457.

(List continued on next page.)

Primary Examiner—Marjorie A. Moran
(74) Attorney, Agent, or Firm—Kenyon & Kenyon

(57) ABSTRACT

The present invention provides vectors and methods which improve the efficiency of nucleic acid insertion into circular vectors, which generally facilitate nucleic acid cloning and specifically facilitate the preparation of DNA libraries. In general, the present invention involves separation of the cloning process into two distinct steps: (a) insertion which is done at a high nucleic acid concentration favoring intermolecular joining, and (b) circularization which is performed at a low nucleic acid concentration favoring intramolecular circularization. The present vectors generally have distinct insertion ends and circularization ends which are blocked from covalent joining during the insertion step. Circularization ends contemplated by the present invention include complementary cohesive ends and topoisomerase-linked ends. The present vectors and methods allow minute amounts of nucleic acid inserts to be efficiently cloned. Moreover, little or no insert size selection occurs with the present methods so that large as well as small nucleic acid inserts are readily inserted into the present vectors. Thus, DNA libraries which are representative of the entire range of size of DNA inserts can be made, and, for example, full length cDNA libraries are readily obtained.

39 Claims, 8 Drawing Sheets

OTHER PUBLICATIONS

Figure 1:
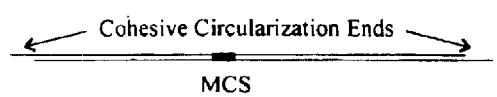
Figure 1:
Figure 1:
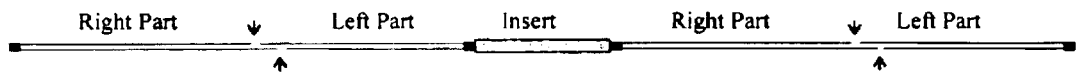
Figure 1:
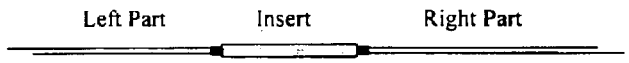
Figure 1:

Sekiguchi J, et al. Vaccinia topoisomerase binds circumferentially to DNA, J Biol Chem. Dec. 16, 1994;269(50):31731–31734.

Shuman S. Novel approach to molecular cloning and polynucleotide synthesis using vaccinia DNA topoisomerase. J Biol Chem. Dec. 23, 1994;269(51):32678–32684.

Shuman S, et al. Site–specific interaction of vaccinia virus topoisomerase I with base and sugar moieties in duplex DNA. J. Biol Chem. Sep. 5, 1993;268(25):18943–18950.

Shuman S. Two classes of DNA end–joining reactions catalyzed by vaccinia topoisomerase I. J Biol Chem. Aug. 25, 1992;267(24):16755–16758.

Shuman S. Site–specific interaction of vaccinia virus topoisomerase I with duplex DNA. MInimal DNA substrate for strand cleavage in vitro. J. Biol Chem. Jun. 15, 1991;266(17):11372–11379.

Aguan K, Kusano T, Suzuki N, Kitagawa Y. An improved method for the construction of high efficiency cDNA library in plasmid or lambda vector Nucleic Acids Res. Feb. 25, 1990;18(4):1071.

Alexander DC, McKnight TD, Williams BG. A simplified and efficient vector–primer cDNA cloning system, Gene. Nov. 1984;31(1–3):79–89.

Andersson B, Wentland MA, Ricafrente JY, Liu W, Gibbs RA. A "double adaptor" method for improved shotgun library construction. Anal Biochem. Apr. 5, 1996;236(1):107–13.

Bellemare G, Potvin C, Simard C, Larouche L. Use of a phage vector for rapid synthesis and cloning of single–stranded cDNA. Gene. 1987;52(1):11–9.

Bellemare G, Protvin C, Bergeron D. High–yeild method for directional cDNA library construction. Gene. Feb. 15, 1991;98(2):231–5.

Boel E. Hjorth AL, Moller KB, Moller PH. A short synthetic adaptor as second–strand primer in the construction of cDNA libraries by the vector–primer method. Biotechniques. Jul. 1991;11(1):26, 28.

Bottger EC. An adaptor strategy to subclone entire cDNA libraries as single insert recombinants. Biotechniques. Oct. 1989;7(9):925–926, 928–929.

Carninci P, Hayashizaki Y. High–efficiency full–lenth cDNA cloning. Methods Enzymol. 1999;303:19–44.

Coleclough C, Erlitz FL. Use of primer–restriction–end adapters in a novel cDNA cloning strategy. Gene. 1985;34(2–3):305–314.

Collins J, Brüning H. Plasmids Useable As Gene–Cloning Vectors In An In Vitro Packaging by Colliphage: Cosmids. Gene. 1978; 4:305–314.

Edwards et al., Oligodesxyribonucleotide litigation to single–strand cDNA: a new tool for cloning 5'ends of mRNAs and for constructing cDNA libraries by in vitro amplification, Nucleic Acids Research, 1991 19(9): 5227–5232.

Gubler U, Hoffman BJ. A simple and very efficient method for generating cDNA libraries. Gene. Nov. 1983;25(2–3):263–269.

Huan RS, Serventi IM, Moss J. Rapid, reliable ligation–independent cloning of PCR products using modified plasmid vectors. Biotechniques. Oct. 1992;13(4):515–518.

Haymerle H, Herz J, Bressan GM, Frank R, Stanley KK. Efficient construction of cDNA libraries in plasmid expression vectors using an adaptor strategy. Nucleic Acids Res. Nov. 11, 1986;14(21):8615–8624.

Heidecker G, Messing J. Sequence analysis of zein cDNAs obtained by an efficient mRNA cloning method. Nucleic Acids Res. Jul. 25, 1983;11(14):4891–4906.

Hu WN, Kopachik W, Band RN. A simple, efficient method to create a cDNA library. Biotechniques. Dec. 1992;13(6):862–864.

Land H, Grez M, Hauser H, Lindenmaier W, Schutz G. 5'–Terminal sequences of eucaryotic mRNA can be cloned with high efficiency. Nucleic Acids Res. May 25, 1981;9(10):2251–2266.

Lang KM, Spritz RA. Cloning specific complete polyadenylylated 3'–terminal cDNA segments. Gene. 1985;33(2):191–196.

MacGillivray RT, Degen SJ, Chandra T, Woo SL, Davie EW. Cloning and analysis of a cDNA coding for bovine prothrombin. Proc Natl Acad Sci U S A. Sep. 1980;77(9):5153–5157.

Norgard MV, Tocci NJ, Monahan JJ. On the cloning of eukaryotic total poly(A)–RNA populations in Escherichia coli. J Biol Chem. Aug. 25, 1980;255(16):7665–7672.

Okayama H, Berg P. High–efficiency cloning of full–length cDNA. Mol Cell Biol. Feb. 1982;2(2):161–170.

Okayama H, Berg P. Bacteriophage lambda vector for transducing a cDNA clone library into mammalian cells, Mol Cell Biol. May 1985;5(5):1136–1142.

Oliner JD, Kinzler KW, Vogelstein B. In vivo cloning of PCR products in E. coli Nucleic Acids Res. Nov. 11, 1993;21(22):5192–5197.

Petty IT, Hunter BG, Jackson AO. A novel strategy for one–step cloning of full–length cDNA and its application to the genome of barley stripe mosaic virus. Gene. Dec. 30, 1988;74(2):423–432.

Pheiffer BH, Zimmerman SB. Polymer–stimulated ligation: enhanced blunt–or cohesive–end ligation of DNA or deoxyribooligonucleotides by T4 DNA ligase in polymer solutions Nucleic Acid Res. Nov. 25, 1983;11(22):7853–7871.

Pruitt SC. Expression vectors permittin cDNA cloning and enrichment for specific sequences by hybridization/selection. Gene. Jun. 15, 1988;66(1):121–134.

Rusche JR, Howard–Flanders P. Hexamine cobalt chloride promotes intermolecular ligation of blunt end DNA fragments by T4 DNA ligase. Nucleic Acids Res. Mar. 25, 1985;13(6):1997–2008.

Sartoris S, Cohen EB, Lee JS. A rapid and improved method for generating cDNA libraries in plasmid and phage lambda vectors. Gene. 1987;56(2–3):301–307.

Schmid A, Cattaneo R, Billeter MA. A procedure for selective full length cDNA cloning of specific RNA species. Nucleic Acids Res. May 26, 1987;15(10):3987–3996.

Spickofsky N, Margolskee RF. A highly efficient directional cDNA cloning method utilizing an asymmetrically tailed linker–primer plasmid. Nucleic Acids Res. Dec. 1991;19(25):7105–7111.

Tseng H. DNA cloning without restriction enzyme and ligase. Biotechniques. Dec. 1999;27(6):1240–1244.

* cited by examiner

1

↓ + Restriction Enzymes + Phosphatase

2

↓ + Insert + Ligase

3

↓ Melting

4

↓ Circularization

5

1 
cos
MCS

↓ + Restriction Enzymes + Phosphatase

2 
Insertion End — cos — Insertion End

↓ + Insert + Ligase

Insert
P⊏────⊐P 3 
cos — Insert — cos

↓ + Terminase 4 
cosR cosL — cosR cosL

↓ Melting

5 
Cohesive End — cosL — cosR — Cohesive End

↓ Circularization 6 
cosL cosR

1

Topoisomerase

Insertion End | Insert | Circularization End    ↓ + Insert

2

↓ + Phosphatase

3

↓ Circularization

4

METHODS FOR INSERTION OF NUCLEIC ACIDS INTO CIRCULAR VECTORS

FIELD OF THE INVENTION

The present invention relates to cloning vectors and improved methods for inserting nucleic acid fragments into circular vectors. The invention further relates to improved methods of DNA library construction. The present vectors and methods allow minute amounts of nucleic acid fragments to be efficiently cloned. Moreover, the vectors and methods of the present invention avoid the size selection problems of currently available vectors and cloning methods. Thus, larger nucleic acid fragments are just as readily cloned using the methods and vectors of the present invention, as are smaller nucleic acid inserts. Accordingly, highly representative libraries can readily be made.

BACKGROUND OF THE INVENTION

Circular vectors are popular and convenient vectors for isolating, maintaining and manipulating nucleic acid fragments. However, currently available methods of nucleic acid insertion into circular vectors have some serious disadvantages. Usually, the desired circular one vector—one insert construct constitutes less than 0.1% of the products when current methods requiring DNA ligation, ligation-independent or topoisomerase joining reactions are used. The remaining 99.9% or more of the products formed include linear concatemers containing multiple vectors and/or multiple inserts. While this efficiency may be sufficient for simple subcloning experiments, it is unacceptable for libraries of complex populations of genomic DNA or cDNA.

One of the major problems of currently used methods is that reaction conditions which are optimized to encourage joining of an insert to a vector tend to discourage circularization of the vector-insert construct. Thus, if the concentrations of vector and insert are sufficiently high, the initial joining of one end of the vector with one end of the insert is a frequent event. However, circularization to form a vector with one insert is problematical because, at this high DNA concentration, the two free ends of the linear vector-insert construct are surrounded by many other DNA ends. Thus, the ends of the vector-insert construct are much more likely to be intermolecularly joined to other DNA ends than to each other. The major products formed are thus linear concatemers containing multiple vectors and/or multiple inserts. On the other hand, at the low DNA concentrations which would tend to facilitate circularization, the initial joining of the vector and insert becomes less likely. Many of the products formed under these conditions are therefore vectors without inserts. Hence, currently used methods are inefficient and can cause vector-to-vector ligation, low efficiency of nucleic acid insertion, and "scrambling" of different nucleic acid fragments, where two or more nucleic acid fragments are joined and inserted into the vector as though they were one fragment. These problems are particularly evident when the cloning reaction involves blunt-ended nucleic acids and complex mixtures of nucleic acids.

To obtain a reasonable number of the desired type of clones, currently used methods generally require optimization of the conditions used for insertion of a fragment into a vector. In practice, this means performing a series of pilot experiments using serial dilutions of each fragment population with each vector type, because optimal cloning conditions depend on the concentration and molar ratio of insert to vector, as well as the lengths of both the vector and fragment insert. No simple formula exists for optimizing the cloning conditions. And if the pilot experiments are not performed, conditions are generally far from optimal, providing only low numbers of clones and unrepresentative libraries.

Moreover, currently used methods strongly select for shorter fragment inserts. This occurs because the ends of longer vector-insert constructs are more likely to become joined to the ends of other vectors or inserts. In contrast, the ends of shorter vector-insert constructs are more likely to find each other and circularize than are the larger vector-insert constructs. The result is unrepresentative libraries which contain a higher proportion of smaller fragments than of larger fragments.

Accordingly, a need exists for new vectors and simplified methods that permit insertion and cloning of nucleic acid fragments and creation of representative DNA libraries.

SUMMARY OF THE INVENTION

The present invention provides a method for inserting a nucleic acid fragment into a circular vector, which includes:

(a) stably joining an insertion end of a nucleic acid fragment with an insertion end of a linearized vector at a first nucleic acid concentration under conditions favoring intermolecular joining, to form a linear vector-insert concatemer;

(b) melting hybridized cohesive circularization ends in said vector-insert concatemer to form a linear vector-insert monomer having single-stranded cohesive circularization ends; and (c) reannealing said single-stranded cohesive circularization ends at a second nucleic acid concentration under conditions favoring circularization to form a circularized vector containing a nucleic acid insert;

wherein said second nucleic acid concentration is more dilute than said first nucleic acid concentration and wherein said cohesive circularization ends are between about 8 and about 50 nucleotides in length.

The present invention also provides a method for inserting a nucleic acid fragment into a circular vector, which includes:

(a) stably joining an insertion end of a nucleic acid fragment with an insertion end of a linearized vector at a first nucleic acid concentration under conditions favoring intermolecular joining, to form a linear vector-insert construct with complementary circularization ends, wherein one or both circularization ends of the vector-insert construct (1) are attached to an enzyme or enzyme complex capable of covalently joining DNA ends, and (2) are blocked from covalent joining;

(b) unblocking said circularization ends of the vector-insert construct; and (c) joining the circularization ends of the insert-vector construct at a second nucleic acid concentration in an intramolecular reaction mediated by the enzyme or enzyme complex under conditions favoring circularization, to form a circularized vector containing a nucleic acid insert;

wherein the second nucleic acid concentration is more dilute than the first nucleic acid concentration.

The present invention is further directed to a nucleic acid insert in a circular vector which is prepared by the present methods. In a preferred embodiment, the present invention provides a genomic library or a cDNA library in a circular vector which is prepared by the present methods.

The present invention also provides a linearized vector which includes an origin of replication, an insertion site, and two complementary cohesive circularization ends, wherein:

each of said cohesive circularization ends is at least about 20 base pairs from said insertion site;

said cohesive circularization ends are between about 8 and about 50 nucleotides in length; and upon hybridization ligase does not substantially covalently join said cohesive circularization ends.

The present invention further provides a linearized vector which includes an origin of replication, a blunt or short sticky insertion end, and a cohesive circularization end, wherein said short sticky insertion end is between 1 and 7 nucleotides in length and said cohesive circularization end is between about 8 and about 50 nucleotides in length.

The present invention also provides a vector including an origin of replication, an insertion end, and a cohesive circularization end, wherein:

said insertion end is covalently linked to a site-specific topoisomerase; and said cohesive circularization end is between about 8 and about 50 nucleotides in length.

The present invention further provides a linearized vector which includes an origin of replication, two insertion ends, and two circularization ends wherein:

each of said circularization ends is located at least 15 base pairs from each of said insertion ends;

each of said insertion ends is covalently linked to a site-specific topoisomerase;

one or both of said circularization ends are covalently linked to a site-specific topoisomerase; and each of said insertion ends and each of said circularization ends has a 5'-phosphate.

The present invention also provides a linearized vector which includes an origin of replication, a bacteriophage or virus cos site, and two insertion ends covalently linked to a site-specific topoisomerase.

The present invention also provides a kit which includes a first compartment containing the linearized vector of the present invention. The kit can also provide another compartment containing a DNA ligase, a terminase, a buffer including polyethylene glycol of high molecular weight, and/or a buffer which includes a salt.

BRIEF DESCRIPTIONS OF THE DRAWINGS

FIG. 1 illustrates ligase-mediated insertion of a DNA fragment ("insert") into the multiple cloning site ("MCS") of a linearized vector which has two cohesive circularization ends. The two cohesive circularization ends are complementary and can hybridize. One or two restriction enzymes are used to cleave the vector in the MCS to create two vector parts, each with an insertion end and a cohesive circularization end. The two vector parts are dephosphorylated with a phosphatase. The 5' phosphate-containing insert is ligated to the insertion ends of two vector parts to form a construct which can be a concatemer of vectors and inserts. Arrows indicate gaps or nicks at the ends of the hybridized cohesive circularization ends which are not covalently closed by the ligase. When the hybridized cohesive circularization ends are melted, vector-insert monomers are released from the concatemer. The vector-insert monomers are circularized under conditions which favor circularization rather than intermolecular joining.

Figure 2:
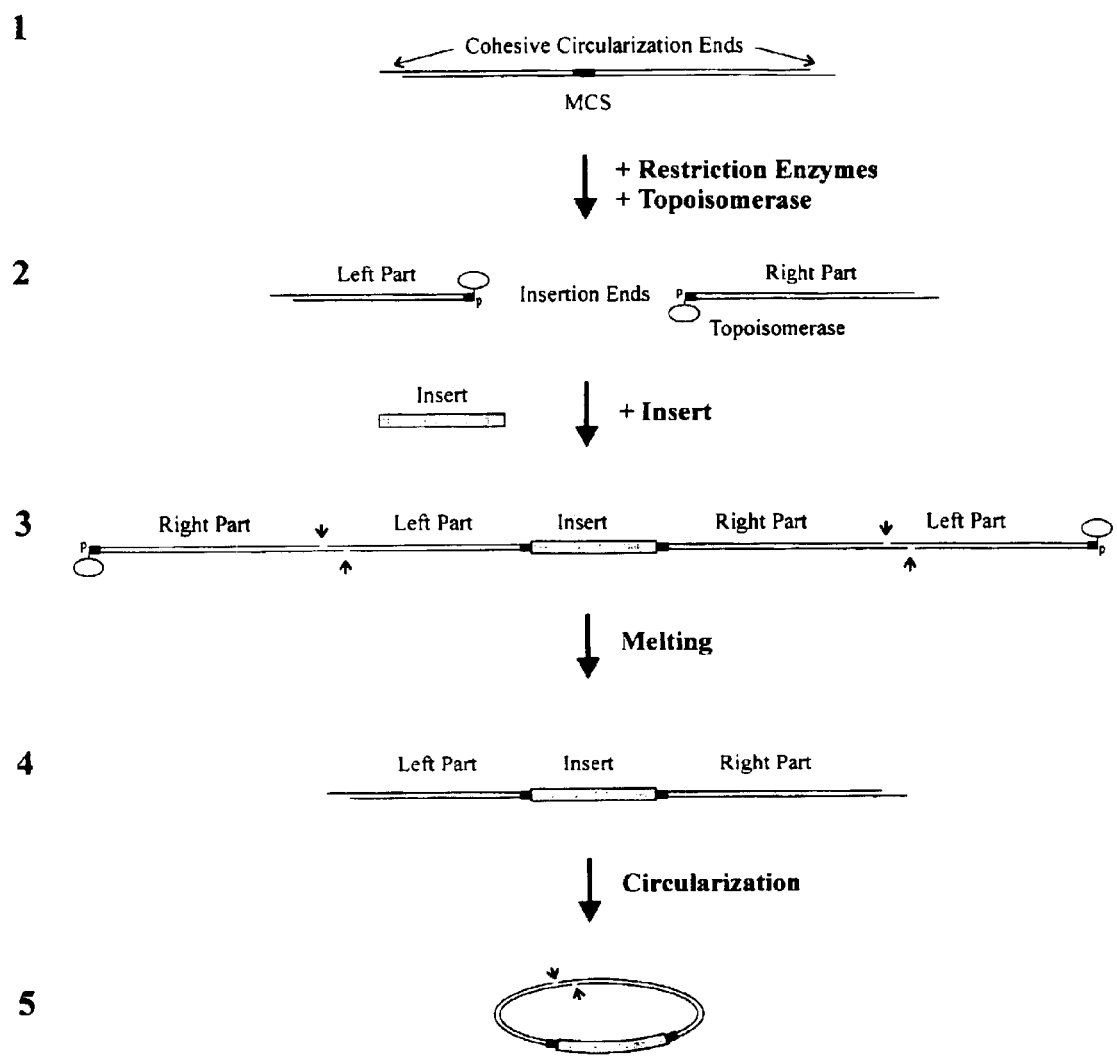

FIG. 2 illustrates another embodiment of the present invention. A dephosphorylated DNA fragment is covalently joined to the insertion ends of a linearized vector, by site-specific topoisomerase molecules which are covalently linked to each insertion end. As in FIG. 1, the vector has two complementary cohesive circularization ends which can hybridize. When the hybridized cohesive circularization ends are melted, the vector-insert monomers are released from the concatemers of vectors and inserts. Each monomer is circularized under conditions favoring circularization.

Figure 3:
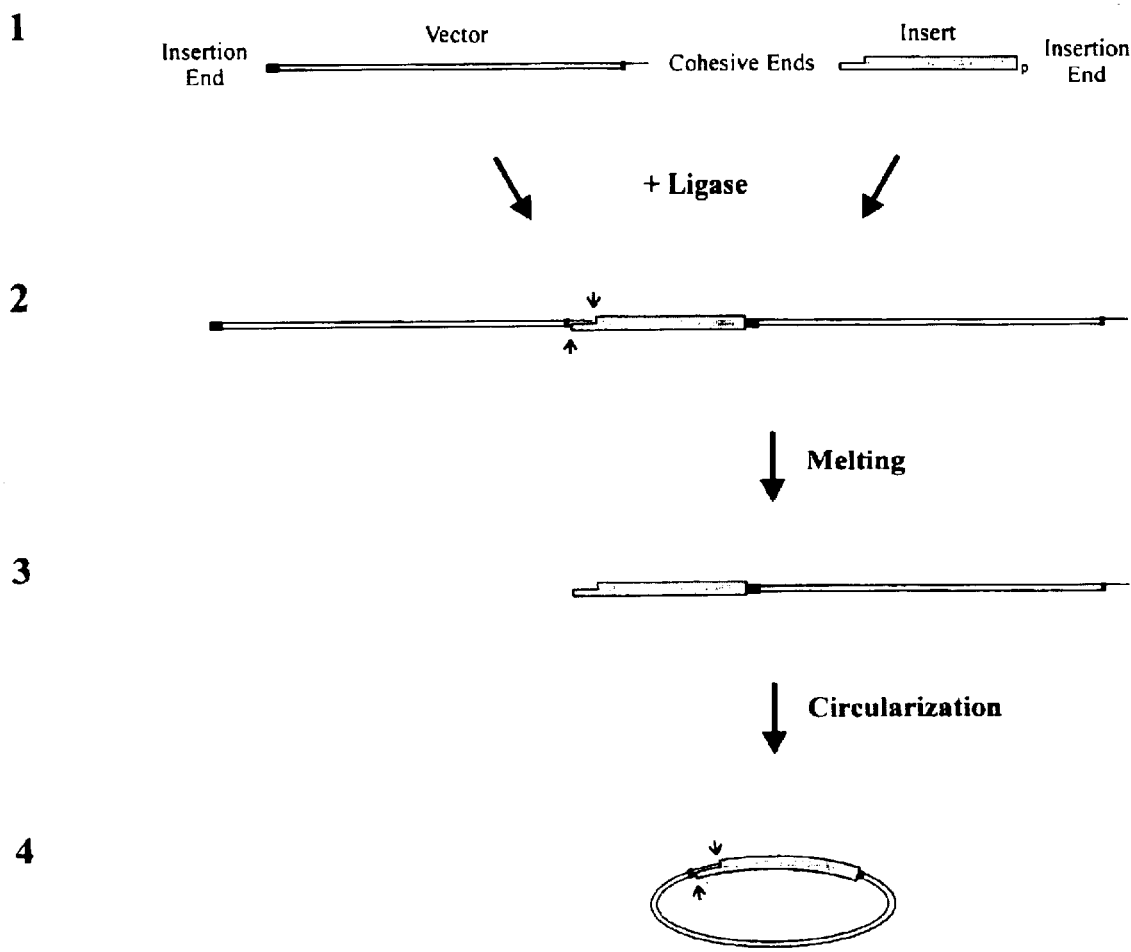

FIG. 3 illustrates ligase-mediated insertion of a DNA fragment with an insertion end and a cohesive circularization end into a linearized vector which has a complementary insertion end and a complementary cohesive circularization end. During ligation of the insertion end of insert with the insertion end of vector, the complementary cohesive circularization ends of vectors and inserts can hybridize, forming linear concatemers. When the hybridized cohesive circularization ends are melted, the vector-insert monomers are released from the concatemers. Each monomer is then circularized under conditions favoring circularization.

Figure 4:
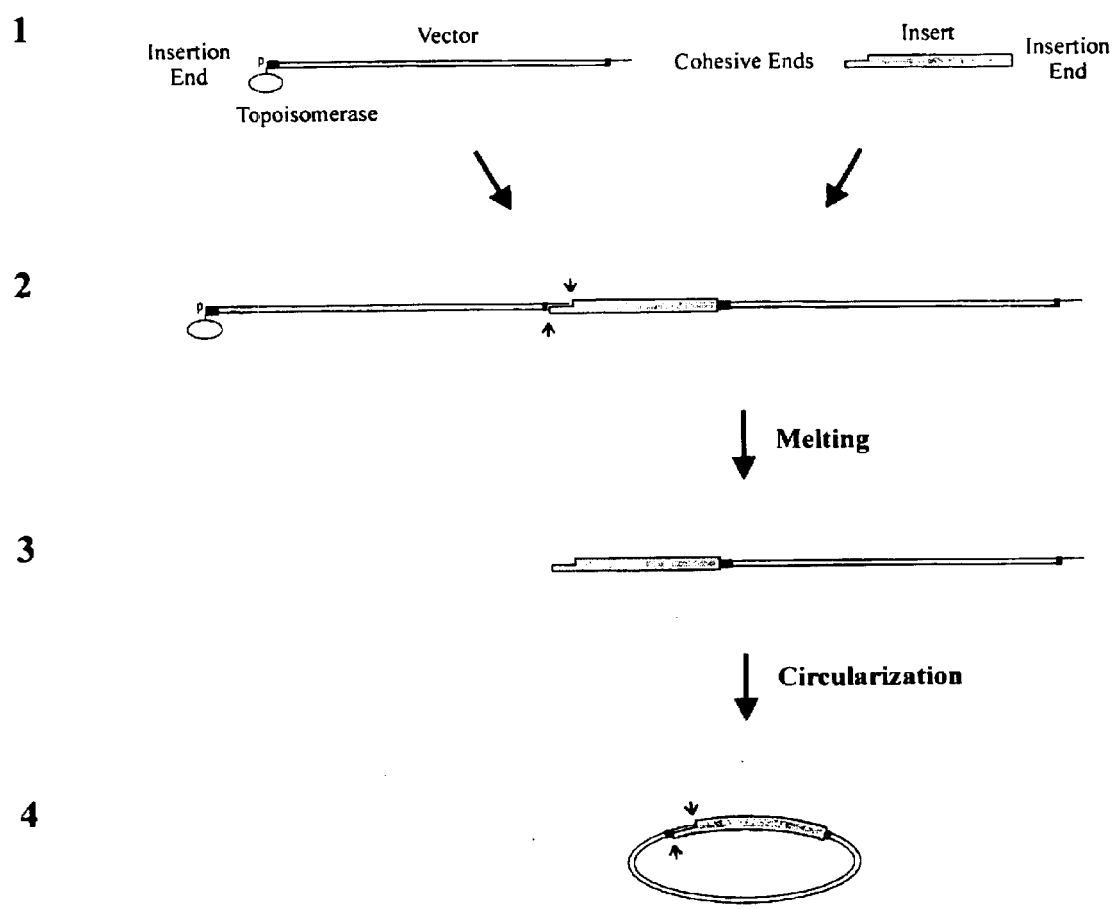

FIG. 4 illustrates a topoisomerase-mediated insertion of a DNA fragment into a linearized vector. The vector has a topoisomerase-linked insertion end and a cohesive circularization end. The insert has a dephosphorylated insertion end and a complementary cohesive circularization end. After topoisomerase-mediated joining of the insertion ends of vector and insert, the cohesive circularization ends of vectors and inserts can hybridize. When the hybridized cohesive circularization ends are melted, the vector-insert monomers are released. Each monomer is then circularized under conditions favoring circularization.

Figure 5:
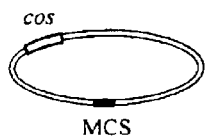
Figure 5:
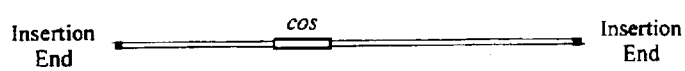
Figure 5:
Figure 5:
Figure 5:
Figure 5:

FIG. 5 illustrates ligase-mediated insertion of a DNA fragment into a linearized vector which contains a bacteriophage cos site. The vector is cleaved in the MCS with one or two restriction enzymes and resulting insertion ends are dephosphorylated. The 5' phosphate-containing insert is ligated to insertion ends of two vectors, forming a concatemer of vectors and inserts. The concatemer is nicked with a terminase at its two recognition sites ("cos" sites), producing cohesive circularization ends which can hybridize. The hybridized cohesive circularization ends are melted to release vector-insert monomers which are circularized under conditions favoring circularization.

Figure 6:
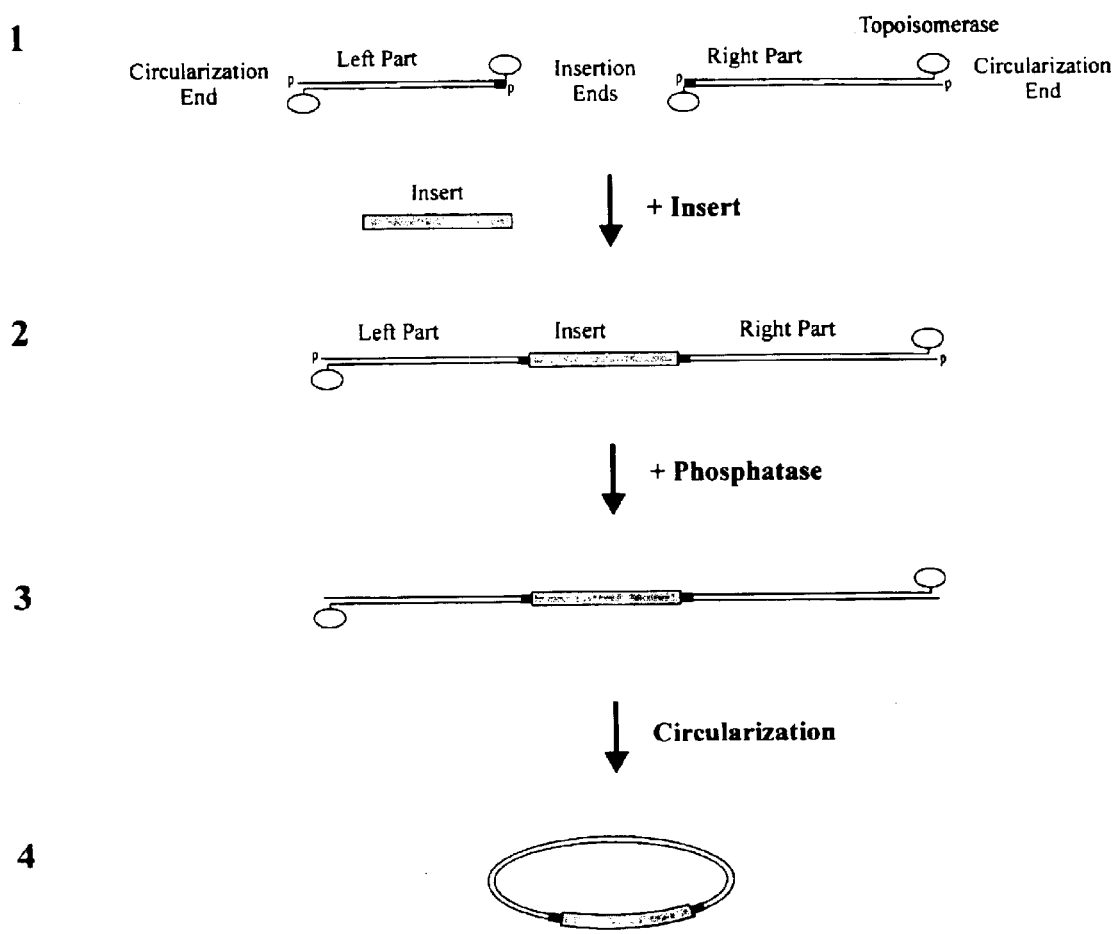

FIG. 6 illustrates insertion of a dephosphorylated DNA fragment into a linearized vector which comprises two vector parts, each having a topoisomerase-linked circularization end and a topoisomerase-linked insertion end. The 5' phosphates on the circularization ends prevent joining of those ends during intermolecular joining of the insert and vector insertion ends, which is mediated by topoisomerase. Thus, linear vector-insert monomers are formed and no monomer separation step is required. The 5' phosphates on the circularization ends are removed by phosphatase. Each vector-insert monomer is circularized by topoisomerase under conditions favoring circularization.

Figure 7:
Figure 7:
Figure 7:
Figure 7:

FIG. 7 illustrates insertion of a DNA fragment into a linearized vector that contains two topoisomerase-linked ends. An insertion end of the fragment insert is dephosphorylated and can be joined to a topoisoinerase-linked end, whereas a circularization end of insert contains 5' phosphate and can not be joined by topoisomerase. After topoisomerase-mediated joining of the insertion end of insert with a vector end, a linear vector-insert monomer is formed. When the 5' phosphate is removed by phosphatase from the circularization end of insert, the vector-insert monomer is circularized by topoisomerase under conditions favoring circularization.

Figure 8:
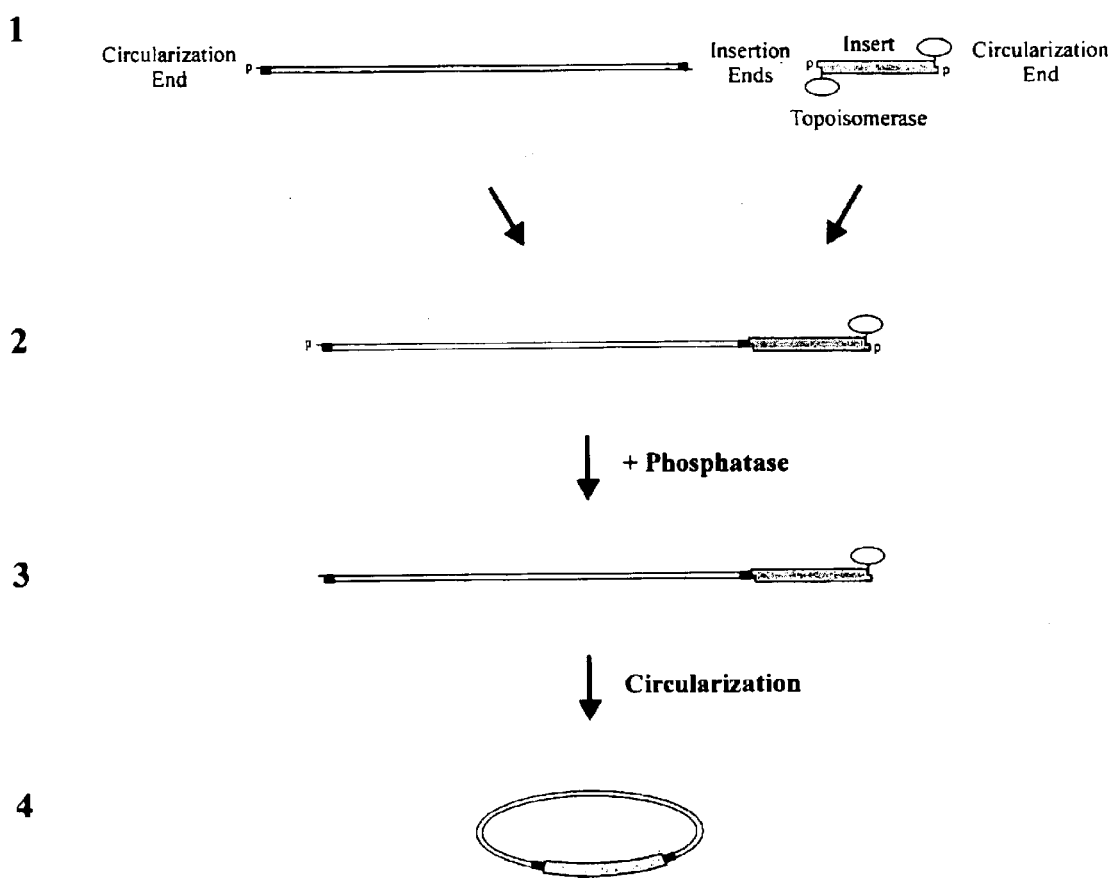

FIG. 8 illustrates insertion of a DNA fragment with two topoisomerase-linked ends into a linearized vector with a 5' phosphate-containing circularization end and a dephosphorylated insertion end. After topoisomerase-mediated joining of the insertion end of vector with the insertion end of insert, a linear vector-insert monomer is formed. When phosphatase removes the 5' phosphate from the circularization end of vector, the vector-insert monomer is circularized by topoisomerase under conditions favoring circularization.

DETAILED DESCRIPTION OF THE INVENTION

The present invention provides vectors and methods for inserting a nucleic acid fragment into those vectors with improved efficiency relative to currently available methods. While currently available methods often result in insertion of less than 0.1% of nucleic acid fragments into a circular vector, the present methods can provide insertion of more than 95% of nucleic acid fragments into the present circular vectors. This high efficiency is provided by the present vectors and methods without the extensive optimization of vector and insert concentrations which is frequently necessitated by currently available vectors and methods. The present vectors and methods are therefore readily used over a wide range of vector and insert concentrations. The present invention is particularly well adapted for handling minute amounts of nucleic acid inserts, which are not efficiently cloned by the available methods. Moreover, while currently available methods strongly select for short nucleic acid fragments, the present invention does not have this size selection problem.

In general, the present invention involves separation of the cloning process into two distinct steps: insertion and circularization. In the insertion step, the linearized vector is joined to the nucleic acid fragment at fairly high nucleic acid concentrations which encourage intermolecular rather than intramolecular joining reactions. In the circularization step, the vector-insert monomers are circularized at comparatively low nucleic acid concentrations that favor intramolecular circularization rather than intermolecular joining. Thus the present invention does not rely upon the rather unlikely event that both ends of a nucleic acid fragment are ligated onto opposite ends of a linearized vector. Instead, the present invention directs the insertion of a nucleic acid into the vector using procedures that promote formation of the desired end product: a circularized vector with a single nucleic acid insert.

According to the present invention, the present vectors have one or two unique circularization ends which are blocked from covalent joining during the insertion step and generally are distinct from the insertion ends. Hence, ligase can be used during the insertion step without formation of a phosphodiester linkage between a circularization end and an adjacent nucleotide. The circularization ends contemplated by the present invention can join to each other the first time those ends meet during the circularization step, without the need for any third molecule or enzyme to migrate to the site of circularization and to facilitate the joining reaction. The circularization ends are fully capable of stable joining without such a molecule or enzyme. This means that the circularization reaction is effectively a bimolecular reaction, because the two ends of the vector-insert monomer migrate relatively independently of each other in solution and therefore can be considered as two molecules. Such bimolecular reaction proceeds more efficiently and at a faster rate than the ligation reaction, which is effectively a trimolecular reaction, because ligation requires the migration of ligase to the site where two nucleic acid ends meet. Circularization ends contemplated by the present invention include but are not limited to complementary cohesive ends and topoisomerase-linked ends.

As used herein, the "cohesive circularization end" is a single-stranded protruding end that is about 8 to about 50 nucleotides in length. Complementary cohesive circularization ends can stably join with each other by hybridization. After hybridizing with a complementary cohesive circularization end, a region of double-stranded nucleic acid is formed, which has a first nick or gap in one strand which is between about 8 and about 50 nucleotides from a second nick or gap in the opposite strand. These nicks or gaps are blocked from covalent closure by any procedure known to one of skill in the art. For example, the circularization end can be de-phosphorylated to prevent formation of a phosphodiester bond by ligase.

The cohesive circularization ends can be melted at high temperatures, but the nicks or gaps do not become substantially covalently closed under most insertion conditions, for example, under conditions used for ligation. The present methods generally do not discourage the formation of concatemers of vectors and inserts during the insertion step. Instead, concatemers formed during the insertion step are separated into vector-insert monomers by melting the cohesive circularization ends. After melting, the vector-insert monomer can be recircularized during the circularization step at low nucleic acid concentrations which favor an intramolecular reannealing of the cohesive circularization ends. Such reannealing of cohesive circularization ends forms a circular vector having a nucleic acid insert.

Thus, the present invention provides a method for inserting a nucleic acid fragment into a circular vector, which includes:

(a) stably joining an insertion end of a nucleic acid fragment with an insertion end of a linearized vector at a first nucleic acid concentration under conditions favoring intermolecular joining, to form a linear vector-insert concatemer;

(b) melting hybridized cohesive circularization ends in the vector-insert concatemer to form a linear vector-insert monomer having single-stranded cohesive circularization ends; and (c) reannealing the single-stranded cohesive circularization ends at a second nucleic acid concentration under conditions favoring circularization to form a circularized vector containing a nucleic acid insert;

wherein the second nucleic acid concentration is more dilute than the first nucleic acid concentration and wherein cohesive circularization ends are between about 8 and about 50 nucleotides in length.

The vectors of the present invention can have insertion and circularization ends which are located at distinct sites, or the fragment can be inserted at a site which has both an insertion end and a circularization end. Thus, in one embodiment, a linearized vector is cleaved in two parts which are at least about 20 base pairs in length, each part containing an insertion end and a cohesive circularization end. The cohesive circularization ends of the two parts can hybridize because they are complementary. In another embodiment, a linearized vector contains an insertion end and a cohesive circularization end. The nucleic acid fragment to be inserted in this vector contains a complementary insertion end and a complementary cohesive circularization end.

Cohesive circularization ends can also be formed after joining the nucleic acid fragment with linearized vector. In another embodiment, a linearized vector has a recognition site for an enzyme or enzyme complex which creates a first nick in one strand which is about 8 to about 50 nucleotides from a second nick in the other strand. After the intermolecular joining, the vector-insert concatemer is nicked with such an enzyme or enzyme complex to produce cohesive circularization ends.

Enzymes or enzyme complexes contemplated for producing cohesive circularization ends which are between about 8 and about 50 nucleotides in length preferably have a specific recognition site which is at least 15 nucleotides in length. If the recognition site is shorter than 15 nucleotides, some nucleic acid fragments can be cleaved, during the construction of a cDNA or genomic library, resulting in a loss of at least a portion of the fragment sequence. In general, restriction enzymes are not used for this purpose because most restriction enzymes have recognition sites of only up to 8 nucleotides in length and/or produce short sticky ends of up to 5 nucleotides in length. The exception is intron-encoded endonucleases, which may be used so long as they have a recognition site which is at least 15 nucleotides in length and provide circularization ends of about 8 to about 50 nucleotides in length.

Other enzymes which can be used to create cohesive circularization ends include bacteriophage or virus terminases, for example, a terminase of bacteriophage lambda which recognizes the lambda cos site and produces 12-nucleotide cohesive ends. Lambda terminase is a component of lambda packaging extract that is used to package cosmids with genomic DNA inserts into lambda phage particles, prior to infection of bacterial cells with these particles. During the packaging process, terminase cleaves the cos site in cosmids and produces cohesive ends. Unlike standard methods of producing cosmids with genomic DNA inserts, however, the present method involves no packaging into phage particles. Instead of infection of bacteria with linearized cosmids containing 30 to 42 kilobase inserts which are packaged into phage particles, the present method involves transfection or electroporation of host cells with circularized vectors containing a wide range of inserts sizes which can be between 20 base pairs and 100,000 base pairs.

In general, formation of the cohesive circularization ends prior to fragment insertion is preferred, so that a uniform preparation of vectors can be made and tested to insure that the cohesive circularization ends are formed. Certain enzymes and enzyme complexes which can be used for making the cohesive circularization ends do not efficiently form the requisite nicks or gaps in their recognition sites. For example, the terminase of lambda bacteriophage may nick neither strand, or only one strand of the lambda cos site, resulting in a reduced efficiency of forming vector-insert monomers if the circularization ends are formed after fragment insertion.

According to the present invention, the cohesive-end duplex is preferably stable at temperatures normally used for transfection or electroporation of the vector into host cells and at temperatures used for incubation of the host cells. However, the melting temperature of the duplex can vary. One of skill in the art can readily control the melting temperature of the present circularization ends, for example, by controlling the salt concentration in the medium and by controlling the length and nucleotide composition of the cohesive circularization ends. The cohesive circularization ends are about 8 to about 50 nucleotides in length. Longer ends of about 20 to about 50 nucleotides will melt at higher temperatures, whereas ends of about 8 to about 20 nucleotides will melt at lower temperatures. Similarly, circularization ends with a higher content of G and C nucleotides will melt at higher temperatures. Preferably, the cohesive circularization ends are composed of at least 50% G and C nucleotides. The cohesive circularization ends can also comprise non-natural nucleotide analogs that have enhanced binding strength and specificity as compared to natural nucleotides. For example, the cohesive circularization ends comprising peptide nucleic acids or nucleoside phosphoramidates can be melted at higher temperatures than the corresponding ends composed of DNA or RNA. The melting temperature can also be controlled by varying the salt concentration of the buffer; the higher the salt concentration, the higher the melting temperature. To avoid excessive heating of DNA, the salt concentration in the melting buffer is preferably between 0 mM and 200 mM. The duplex is preferably stable at 37° C. and up to about 42° C. However, at higher temperatures the duplex formed by the cohesive circularization ends melts, for example, at temperatures between about 45° C. and about 80° C. In a preferred embodiment, the duplex is melted at temperatures between about 50° C. and about 75° C.

To effect circularization, the linear vector-insert monomers are diluted in a large volume of a circularization buffer and circularized by reannealing the cohesive circularization ends. Dilution insures that each monomer is sufficiently far from other nucleic acids to prevent intermolecular hybridization during reannealing. Instead, intramolecular joining (circularization) is favored. Reannealing preferably proceeds at a temperature that is 5° to 10° C. below the melting temperature of the cohesive circularization ends. A higher circularization temperature increases the rate of diffusion of DNA ends and results in a shorter average time of circularization. If a high circularization temperature is desired, for example, for construction of cDNA libraries by the present methods, the salt concentration in the circularization buffer can be increased, compared to the melting buffer. For example, the circularization buffer can contain 2.5 M ammonium acetate, whereas the melting buffer can contain no salt. In a preferred embodiment, the circularization temperature is between about 50° C. and about 85° C. In a more preferred embodiment, circularization is performed at about 60° C. to about 75° C. After reannealing, the circularized vectors with inserts can be precipitated and purified by standard procedures to facilitate transfection or electroporation into a host cell.

The present invention contemplates any host cell used by one of skill in the art for maintaining or replicating circular vectors. Such host cells can be prokaryotic or eukaryotic cells. For example, such host cells can be $E.\ coli$, yeast, insect, mammalian, or any other cell type. However, in a preferred embodiment, the host cell is prokaryotic.

The present circular vectors, which either contain or do not contain a nucleic acid fragment insert, can be introduced into a host cell of the present invention by any available procedure, for example, by transfection, micro injection or electroporation. After maintaining or replicating the present vectors, with or without nucleic acid fragment inserts, the vectors can be recovered and purified by any procedures known to one of skill in the art. See, e.g., Sambrook et al., Molecular Cloning: A Laboratory Manual, Vol. 1–3 (Cold Spring Harbor Press, Cold Spring Harbor, N.Y.), 1989.

A significant advantage of the present vectors and methods is that circularization proceeds as a bimolecular reaction, wherein two ends of a linear vector-insert construct are considered as independent molecules. The cohesive circularization ends stably anneal as soon as they find each other in solution. In contrast, ligation requires a ligase molecule to be present in the same location where two DNA ends meet. This means that ligation reactions are effectively trimolecular reactions. Because the concentration of ligase can not be so high that ligation occurs every time two DNA ends meet, only a small percentage of DNA end meetings result in ligation. If, for example, ligation happens only in one out of a hundred DNA end meetings, the efficiency of circularization by ligation is a hundred times less than the efficiency of circularization by a bimolecular reaction at the same temperature. Importantly, the longer a vector-insert construct, the longer the time between end meetings. The dependence of time on the length of the construct is non-linear: at temperatures normally used for ligation, it can be minutes for short inserts but up to hour for long inserts. If ligation occurs in one out of a hundred DNA end meetings, the average time of circularization can be from hours for short inserts to days for long inserts. Therefore, the repeated cycles of meeting and separation of DNA ends over a period of time normally used for ligation (up to 20 hours) result in circularization of almost all vectors with short inserts, but a majority of vectors with long inserts will not be circularized. In contrast, the present methods provide circularization of substantially all present vectors with short as well as long inserts. Moreover, the present circularization reaction occurs within several hours of incubation at the contemplated high temperatures which facilitate diffusion of cohesive circularization ends. Thus, the methods and vectors provided by the present invention enable the creation of DNA libraries which contain the entire spectrum of nucleic acid fragment sizes constituting the total library. Unlike the currently available cloning procedures, the present methods and vectors have substantially no selection favoring the insertion of small nucleic acid fragments into the vector.

The circularization can be mediated not only by hybridization of complementary cohesive ends, but also by an enzyme-mediated reaction. However, unlike commonly used ligation enzymes, the enzymes contemplated by the present invention can become stably attached to one or both circularization ends prior to a covalent joining of two circularization ends. Because a complex of such an enzyme with a circularization end migrates in solution as one molecule, circularization proceeds as a bimolecular reaction.

One example of such an enzyme is a site-specific topoisomerase I.

Topoisomerases are a class of enzymes that modify the topological state of DNA by breaking and rejoining DNA strands. Topoisomerases contemplated by the present invention recognize a specific DNA sequence and can cleave one strand at such a recognition site, becoming covalently attached to a 3' phosphate of the cleaved strand. The presently contemplated topoisomerases can also join the 3' phosphate with a 5'-OH end of the originally cleaved strand or with a 5'-OH end of the heterologous acceptor DNA. However, when a 5'-phosphate is present on the acceptor DNA, the topoisomerase can not join the ends. Topoisomerases with these characteristics include viral topoisomerases such as poxvirus topoisomerases. Examples of poxvirus topoisomerases include Vaccinia virus, Shope fibroma virus, ORF virus, and Amsacta moorei entomopoxvirus topoisomerases that bind to a pentanucleotide recognition site and cleave after the last base: (C/T)CCTT↓. Other site-specific topoisomerases possessing these characteristics may be known to those skilled in the art and are contemplated herein. In a preferred embodiment, the site-specific topoisomerase is Vaccinia topoisomerase I or Vaccinia topoisomerase I fusion protein.

The present invention uses the fact that topoisomerase can not join the 3'-phosphate, to which it is covalently attached, with a 5'-phosphate-containing end of acceptor DNA. Thus, circularization can be controlled by adding and removing 5'-phosphates. The 5' phosphate blocks the joining of circularization ends during the insertion step, when only insertion ends of the vector and nucleic acid fragment are joined. Only after the removal of the 5'-phosphate, can topoisomerase join the circularization ends in an intramolecular reaction. Preferably, the linear vector-insert monomers are diluted in a large volume of a circularization buffer prior to the addition of a dephosphorylation enzyme to provide favorable conditions for circularization, because earlier removal of 5' phosphates may permit intermolecular joining rather than circularization.

Other enzymes known to one of skill in the art which can become covalently or non-covalently attached to a circularization end and are capable of joining two DNA ends are contemplated by the present invention. For example, such an enzyme may attach to DNA by hydrogen bonding or by recognition of a terminal phosphate or hydroxy group. Such enzyme could be, for instance, a ligase which, unlike commonly used ligases such as T4 DNA ligase or *E. coli* DNA ligase, can become stably attached to one DNA end prior to joining it to a second DNA end. Because a complex of a circularization end with such ligase migrates in solution as one molecule, circularization can proceed as a bimolecular reaction. To prevent covalent joining of circularization ends during the insertion step, the circularization ends can be blocked, for example, by dephosphorylation. Addition of 5' phosphates by a kinase, such as T4 polynucleotide kinase, preferably under diluted conditions, will render a ligase which is attached to one or both circularization ends capable of joining those ends in an intramolecular reaction.

The present invention provides a method for inserting a nucleic acid fragment into a circular vector, which includes:

(a) stably joining an insertion end of a nucleic acid fragment with an insertion end of a linearized vector at a first nucleic acid concentration under conditions favoring intermolecular joining, to form a linear vector-insert construct with complementary circularization ends, wherein one or both circularization ends of the vector-insert construct (1) are attached to an enzyme or enzyme complex capable of covalent joining DNA ends, and (2) blocked from the covalent joining:

(b) unblocking the circularization ends of the vector-insert construct; and (c) joining the circularization ends of the insert-vector construct at a second nucleic acid concentration in an intramolecular reaction mediated by the enzyme or enzyme complex under conditions favoring circularization, to form a circularized vector containing a nucleic acid insert;

wherein the second nucleic acid concentration is more dilute than the first nucleic acid concentration.

In a preferred embodiment, the enzyme or enzyme complex is a site-specific topoisomerase that is covalently linked through a 3' phosphate to a circularization end, and the topoisomerase does not substantially covalently join the circularization ends of the vector-insert construct until the 5'-phosphates are removed from the circularization ends.

In one embodiment, the linearized vector is cleaved in two parts at least about 15 base pairs in length, each of which contains an insertion end and a circularization end, wherein one or both of the circularization ends are covalently linked through a 3' phosphate to a site-specific topoisomerase. In another embodiment, a linearized vector contains an insertion end and a circularization end, whereas a nucleic acid fragment contains a complementary insertion end and a complementary circularization end, wherein either the circularization end of the vector or the circularization end of the nucleic acid fragment is covalently linked through a 3' phosphate to a site-specific topoisomerase.

The 5' phosphates can be removed by any dephosphorylation enzyme, for example, an alkaline phosphatase such as calf intestinal phosphatase. Preferably, a thermolabile phosphatase is used, which can be inactivated by heating to about 65° C. prior to transfection or electroporation of vectors with inserts into host cells. Such thermolabile phosphatases include shrimp alkaline phosphatase and HK™ alkaline phosphatase (Epicentre) derived from an Antarctic bacterium. Other thermolabile phosphatases may be known to those skilled in the art.

The present methods generally employ one of the present vectors which has been cleaved at the insertion site. The cleavage site created by linearization should generate DNA ends which are compatible with the ends of the DNA fragment to be inserted into the vector. Either one or two cleavages can be made at the insertion site. Cleavage with one restriction enzyme yields a vector with blunt or complementary sticky ends. One of skill in the art can readily select the appropriate enzymes and procedures to cleave the present vectors. See Sambrook et al., 1989 Molecular Cloning: A Laboratory Manual, Vol. 1–3 (Cold Spring Harbor Press, Cold Spring Harbor, N.Y.).

The nucleic acid fragment can be any nucleic acid, for example, any eukaryotic, prokaryotic, viral or bacteriophage nucleic acid. The nucleic acid can be genomic DNA, cDNA, RNA:DNA hybrid, or a nucleic acid containing nucleotide analogs. The nucleic acid can be a polymerase chain reaction (PCR) product, an oligonucleotide, an adapter, or a part of a vector.

An intermolecular joining reaction (insertion step) can be performed by any procedure available to one of skill in the art, for example, by ligation, ligation-independent or topoisomerase-mediated procedures. Ligation employs a ligation enzyme, for example, T4 DNA ligase. Ligation-independent joining is based on annealing a cohesive insertion end of a linearized vector to a complementary cohesive insertion end of a nucleic acid fragment. Topoisomerase-mediated joining is performed by a site-specific topoisomerase I covalently linked to a 3' phosphate of an insertion end. Topoisomerase can be linked to one or both insertion ends of vector or to one or both ends of a nucleic acid fragment. Upon contact of a topoisomerase-linked end with an appropriate dephosphorylated end, topoisomerase covalently joins the two ends and dissociates. Any type of site-specific topoisomerase I possessing these properties can be used, for example, Vaccinia topoisomerase I or a Vaccinia topoisomerase I fusion protein.

The available methods of topoisomerase-mediated DNA cloning into circular vectors, for example, TOPO™ cloning method commercialized by Invitrogen, have a time limitation for the cloning reaction. The maximum amount of clones is obtained after a 5 minute incubation at room temperature, whereas incubations longer than 5 minutes result in the reduction of the amount of clones. The probable reason for this reduction is the formation of linear concatemers of vectors and inserts. In the TOPO™ cloning method, circularization of linear vector-insert monomers is likely to occur only after transfection into bacterial cells, because topoisomerase is still attached to the vector's end. The recommended conditions for TOPO™ cloning include a molar ratio of a nucleic acid to vector that is higher than 1:1. The amount of linear vector-insert monomers may reach a maximum after a 5 minute incubation, with a prolonged incubation resulting in the accumulation of linear insert-vector-insert and longer concatemers. In contrast, the methods and vectors of the present invention employing topoisomerase-mediated insertion and/or circularization reactions do not have a time limitation. Both insertion and circularization steps can be as long as required to achieve nearly 100% efficiency, for example, circularization can be performed overnight. Moreover, the TOPO™ cloning method has an additional mechanism of selection for shorter inserts. If topoisomerase-mediated circularization of linear vector-insert monomers occurs inside bacterial cells, bacterial nucleases can digest such linear monomers before they are circularized. Since longer vector-insert monomers require a longer circularization time, they have higher chances to be digested than shorter vector-insert monomers. The methods and vectors of the present invention do not have this problem: both insertion and circularization reactions are performed in a nuclease-free environment in vitro.

According to the present invention, the intermolecular joining of the vector and nucleic acid fragment is performed under conditions that discourage recircularization of a vector without insert and formation of covalently linked arrays of vector. If the intermolecular joining is mediated by ligase, such conditions include removal of the 5' phosphates from the linearized vector's ends using a dephosphorylation enzyme, for example, an alkaline phosphatase. If the intermolecular joining is mediated by topoisomerase, the vector's ends preferably retain the 5' phosphates.

Preferably, the intermolecular joining is performed under conditions that promote the insertion of only one nucleic acid fragment into the circular vector, because joining of two or more different DNA fragments can lead to the misperception that those DNA fragments are naturally adjacent to one another, for example, in the genome. Such conditions include a molar excess of the vector relative to the nucleic acid fragment. In a preferred embodiment, the molar ratio of vector to nucleic acid fragment is about 2:1 to about 100,000,000:1. In a more preferred embodiment, the molar ratio of vector to nucleic acid fragment is about 5:1 to about 1,000,000:1. In a still more preferred embodiment, the molar ratio of vector to nucleic acid fragment is about 20:1 to about 1,000:1. For example, if such molar ratio is 20:1, then about 95% of circularized vectors will contain only one nucleic acid fragment. If such ratio is 1,000:1, about 99.9% of circularized vectors will contain only one nucleic acid fragment. In the available cloning methods, the low efficiency of DNA insertion into circular vectors generally does not permit increases in molar ratio of vector to insert of more than about 10:1, and the recommended ratio often is about 1:1, resulting in frequent insertion of two or more different DNA fragments into a circular vector.

To increase the efficiency of intermolecular joining, macromolecular crowding preferably can be used. Macromolecular crowding has been used for DNA ligation into bacteriophage lambda, but has not generally been used with circular vectors, because it produces linear concatemers containing multiple vectors and inserts and almost no circular vector-insert constructs. In contrast to available methods, the present methods benefit from the formation of concatemers of vectors and inserts during the insertion step. Macromolecular crowding provides a large reduction in the effective volume of reaction by using water-binding macromolecules, such as polyethylene glycol 8,000, Ficoll 400,000, bovine serum albumin, and the like. At the conditions of macromolecular crowding, the first nucleic acid concentration referred herein has to be calculated for the effective volume of reaction rather than for the physical volume. The reduction in volume concentrates nucleic acid molecules and enzymes, bringing them into close proximity and resulting in a significant increase in the speed of enzymatic reactions such as DNA ligation. For example, over 90% of even blunt-ended nucleic acid fragments may be ligated to vector ends at the conditions of macromolecular crowding, but the blunt-end ligation is very inefficient at normal ligation conditions. Thus, the efficiency of intermolecular joining is at least about 90% and can be as high as 99%.

The efficiency of circularization of the present vectors with inserts can be equally high. A bimolecular circularization reaction generally provides stable joining of the two ends of a vector-insert monomer the first time when the ends meet in solution. In the cohesive-end-mediated present methods, the present invention contemplates the use of high salt concentrations, for example, between about 2.5 M and about 7.5 M ammonium acetate, which enables to achieve high circularization temperatures, for example, between about 65° and about 85° C. Such high circularization temperatures in turn accelerate the rate of diffusion and decrease the average circularization time. With a sufficiently long incubation at a high circularization temperature, substantially all vectors with short as well as long inserts become circularized. For example, if circularization is performed at 75° C. for 8 hours in a buffer containing 2.5 M ammonium acetate, the efficiency of circularization is substantially the same over a range of insert sizes varying from about 20 base pairs to about 20,000 base pairs. Thus, the methods and vectors provided by the present invention enable the creation of representative DNA libraries in circular vectors, for example, cDNA and genomic libraries. However, the length of nucleic acid fragments that can be inserted into the present vectors by the present methods is not limited to 20,000 base pairs, and can be as long as 100,000 base pairs.

Viral topoisomerases possessing the desired properties that described herein are thermolabile enzymes and generally are substantially inactivated during a prolonged incubation at temperatures above about 60° C. For example, the temperature of Vaccinia topoisomerase-mediated circularization preferably is between about 20° C. and about 50° C. Thus, the rate of diffusion and correspondingly the rate of circularization generally can be lower for topoisomerase-mediated present methods than for cohesive-end-mediated present methods that can afford significantly higher circularization temperatures. For DNA library construction, the cohesive-end-mediated present methods currently are preferred. However, heat-stable site-specific topoisomerases may be found, for example, in organisms living at elevated temperatures, such as those found in hot springs. Their application for circularization of vector-insert monomers at temperatures between about 50° C. and about 85° C. is contemplated by the present invention.

The high efficiencies of the intermolecular joining and circularization of the present methods enable very small amounts of nucleic acid fragments to be cloned in the present vectors. For example, as little as about $10^{-21}$ mole of a nucleic acid fragment can be cloned by the present methods. Unlike available methods, the present methods do not require optimization of the concentrations of either the present vectors or nucleic acid fragments. The present methods are equally efficient over a wide range of nucleic acid fragment concentrations. For example, between about $10^{-21}$ mole and about $10^{-14}$ mole of fragment can readily be cloned by the present methods. An additional benefit of the high efficiency of the present methods and vectors is that only small amounts of vector and nucleic acid DNA, and correspondingly of DNA/RNA modifying enzymes, polymerases and restriction enzymes, are generally required. This can significantly reduce the expense of cloning.

The present methods and vectors are particularly well suited for construction of representative cDNA and genomic libraries from a limited amount of starting material, for example, as little as 1 ng of poly(A)+ RNA. This is a major improvement relative to the available methods of cDNA library construction.

Two general approaches exist for constructing cDNA libraries in a circular vector. One approach relies on the first strand cDNA synthesis primed with an oligo(dT) oligonucleotide, followed by the second strand synthesis and ligation of the double-stranded cDNAs with a linearized vector. This approach suffers from the general shortcomings of ligation-mediated cloning, such as a low efficiency of forming circular vector-insert constructs and a strong selection for shorter inserts.

The second approach uses a "vector primer" where the first strand cDNA synthesis is primed with an oligo(dT) extension on the linearized vector. Because a vector-primer is significantly larger than an oligo(dT) oligonucleotide, its molar concentration during the cDNA synthesis is generally substantially lower than the molar concentration of the oligo(dT) oligonucleotide. Therefore only a relatively small percentage of poly(A)+ RNA becomes converted into double-stranded cDNA by the vector-primer method, whereas oligo(dT) oligonucleotide priming helps convert substantially all poly(A)+ RNA into double-stranded cDNA. Macromolecular crowding and other methods of facilitating the annealing of vector-primer molecules with poly(A) tails of mRNA do not solve this problem. Because RNA is a single-stranded molecule, macromolecular crowding results in annealing of different RNA molecules together which strongly impedes cDNA synthesis. In contrast, the present methods and vectors can benefit both from a high efficiency of cDNA priming by oligo(dT) oligonucleotide, and from a high efficiency of intermolecular joining, and from a high efficiency of bimolecular circularization.

The present methods employing bimolecular circularization of vector-insert monomers could be modified to perform a trimolecular circularization mediated by ligation. For instance, a vector could be cut by a restriction enzyme outside of the insertion site and dephosphorylated. Alternatively, both ends of a vector and one end of a nucleic acid fragment could be dephosphorylated. Following intermolecular joining of the insertion ends, the dephosphorylated circularization ends could be treated with T4 polynucleotide kinase and circularized by a DNA ligase. However, as explained herein, such methods would suffer from a strong selection for shorter inserts and thus could not be used for cloning a variety of nucleic acid fragments. Several additional enzymatic treatments and long circularization times are among other disadvantages of ligation-mediated circularization, increasing both the time and expense of cloning compared to the methods and vectors of the present invention.

The present invention also provides vectors for insertion of nucleic acid fragments by the present methods. The present vectors include any circular DNA vector, for example, plasmids, cosmids, phagemids, circular DNA viruses, and the like. The circular vector should have an origin of replication and at least one insertion site. The origin of replication allows the vector to be maintained and replicated in a prokaryotic or eukaryotic host cell. For many of the methods of the present invention, a prokaryotic host cell is preferred, and a prokaryotic origin of replication should be present on the circular vector to permit replication in such prokaryotic host cells. An insertion site usually is represented by a restriction site which generally is cleaved with the corresponding restriction enzyme prior to the insertion of a nucleic acid fragment. One of skill in the art can readily prepare a circular vector with such an origin of replication and with at least one insertion site, using available methods. See, e.g., Sambrook et al., Molecular Cloning: A Laboratory Manual, Vol. 1–3 (Cold Spring Harbor Press, Cold Spring Harbor, N.Y.), 1989.

In one embodiment, the present invention provides a linearized vector which includes an origin of replication, an insertion site, and two complementary cohesive circularization ends, wherein each of the cohesive circularization ends is at least about 20 base pairs from the insertion site and the cohesive circularization ends are between about 8 and about 50 nucleotides in length.

The present vector can be cleaved in the insertion site with at least one restriction enzyme and the resulting insertion ends can be further treated to prepare them for intermolecular joining. In one embodiment, intermolecular joining is performed by ligation. In this embodiment, the cohesive circularization ends can be blocked so that they generally do not get covalently closed during ligation. For example, to prevent covalent closure of the cohesive circularization ends, one or a few nucleotide gaps can be placed in one strand at about 8 to about 50 nucleotides from a similar gap in the other strand. Alternatively, 5' phosphates can be removed from the cohesive circularization ends or 3' phosphates added to the ends. Any other method commonly used by one of skill in the art to block such DNA ends from ligation is contemplated by the present invention. Hence, the nicks or short gaps flanking the cohesive circularization ends are maintained so the cohesive circularization ends can be repeatedly melted and reannealed. When the vector is placed into a host cell, the nick or short gap is generally repaired, creating an intact, covalently closed vector. The insertion ends preferably are dephosphorylated, to prevent vector-to-vector ligations.

In another embodiment, intermolecular joining is performed by a site-specific topoisomerase covalently attached to each of the insertion ends. The present invention provides a linearized vector which includes an origin of replication, two complementary cohesive circularization ends, and two insertion ends covalently attached to a site-specific topoisomerase, wherein the cohesive circularization ends are between about 8 and about 50 nucleotides in length and wherein each of the cohesive circularization ends is at least about 20 base pairs from each of the insertion ends. In a preferred embodiment, the topoisomerase is Vaccinia topoisomerase or Vaccinia topoisomerase-fusion protein.

Blocking the cohesive circularization ends or gap formation are generally necessary only when ligase is used for DNA fragment insertion. Blocking and gap formation are not necessary when topoisomerase is used.

According to the present invention, the cohesive circularization ends can hybridize together to form a duplex that is stable at temperatures normally used for transfection or electroporation of the vector into host cells. Preferably, the cohesive circularization ends are composed of at least 50% G and C nucleotides.

In general, any available methods can be used for making the present cohesive circularization ends. Cohesive circularization ends can be created, for example, by first cutting a circular vector with one or two restriction enzymes in a location outside of the intended insertion site. In one embodiment, oligonucleotide adapters are ligated onto the resulting vector ends. In another embodiment, nucleotides can be added to the resulting vector ends, for example, by terminal transferase. Then, one tailed DNA end can be removed and an oligonucleotide adapter which is complementary to the remaining tail can be added.

In another embodiment, the cohesive circularization ends can be made using two direct repeats, composed of either only G/C residues or only A/T residues and separated by a restriction site. The direct repeats can be inserted into a location outside of the intended insertion site. After digestion with a corresponding restriction enzyme, cohesive circularization ends are formed by removing nucleotides from one strand of each end. The removal of nucleotides up to a specific nucleotide can be precisely controlled by using a proofreading activity of some DNA polymerase, for example T4 DNA polymerase, in the presence of only one or two dNTPs. Alternatively, the nucleotides can be removed from one strand of each end in a somewhat less-controlled manner, using a 3'-5' or 5'-3' exonuclease.

In another embodiment, the vector can be amplified by the inverse PCR procedure with partially complementary primers that are oriented in opposite directions, followed by removal of nucleotides using the proofreading activity of some DNA polymerase or using a 3'-5' or 5'-3' exonuclease. If the primers used for inverse PCR contain dUMP residues, uracil DNA glycosylase can be used to remove those deoxyuracil residues, disrupting base-pairing and exposing single-stranded cohesive circularization ends. Additionally, abasic sites formed by the removal of deoxyuracil residues can be cleaved by Endonuclease IV.

In another embodiment, the cohesive circularization ends can be formed by cleaving a recognition site in the vector with an enzyme or enzyme complex that produces a first nick in one strand of the vector at about 8 to about 50 nucleotides from a second nick in the other strand. In general, restriction enzymes are not used for this purpose because the sticky ends produced by restriction enzymes generally are not long enough to form useful cohesive circularization ends. One example of restriction enzyme that produces 9-base 3' overhangs is TspR I. The recognition site of TspR I is a pentanucleotide CA(C/G)TG which can be found in a nucleic acid sequence on average every 512 nucleotides. If a vector has more than one TspR I site, the extra sites have to be eliminated prior to the digestion of the vector with TspR I in order to produce cohesive circularization ends. Other restriction enzymes that produce cohesive ends at least about 8 nucleotides in length may be known to those skilled in the art and are contemplated herein. Other enzymes which can be used to create cohesive circularization ends include bacteriophage or virus terminases, for example, a terminase of lambda bacteriophage which recognizes the lambda cos site and produces 12-nucleotide cohesive ends.

An insertion end covalently linked to a site-specific topoisomerase can contain a 5' overhang, a 3' overhang, or a blunt end. A 5' overhang can be readily made by a method described by S. Shuman in J. Biol. Chem. 269, 32678–32684, 1994. In this method, a recognition site for a site-specific topoisomerase, for example, Vaccinia topoisomerase I, is inserted at a distance of between 2 and 10 nucleotides from the end of a double-stranded DNA. Topoisomerase cleaves one strand after its recognition site and forms a covalent bond with a 3' phosphate, whereas the downstream portion of the cleaved strand dissociates from the DNA-topoisomerase complex.

A blunt end with a covalently attached site-specific topoisomerase can be produced if, prior to treatment with topoisomerase, a nick is introduced across from the topoisomerase cleavage site. See Shuman, 267 J. Biol. Chem., 16755–16758 (1992). In one embodiment of the present invention, such a nick can be introduced by DNA cleavage with a restriction enzyme, followed by ligation to a double-stranded oligonucleotide adapter. Preferably, a restriction enzyme that cleaves DNA at some distance from its site is used. Examples of commercially available restriction enzymes with these characteristics include, but are not limited to, Bbs I, Bbv16 II, Bcg I, Bpi I, Bpm I, BpuA I, Bsa I, BseR I, Bsg I, BsmA I, BsmB I, BspM I, BsrD I, Eam1104 I, Ear I, Eco31 I, Eco57 I, Esp3 I, Gsu I, Ksp632 I, Sap I. Other restriction enzymes with these characteristics are known to those skilled in the art and are contemplated herein. The recognition site for such a restriction enzyme is positioned so that the restriction enzyme cleaves DNA exactly opposite to a cleavage site of the topoisomerase. For example, if restriction enzyme Bbs I and Vaccinia topoisomerase I are used, the GAAGAC recognition site of Bbs I can be placed one nucleotide before the CCCTT recognition site of Vaccinia topoisomerase I. After digestion with Bbs I, the DNA end is ligated to a double-stranded oligonucleotide adapter with a 5' phosphate-containing sticky end complementary to the sticky end left by digestion with Bbs I. The second strand of the adapter is blocked from ligation to the 5' phosphate-containing DNA end, resulting in a nick opposite to a topoisomerase cleavage site. Such blocking can be achieved, for example, by placing a phosphate group on the 3' end of the second strand of the adapter. Other ways of blocking 3' end from ligation are known to those skilled in the art and are contemplated herein. Alternatively, only the 5' phosphate-containing oligonucleotide is present during ligation reaction, and the complementary oligonucleotide is annealed to it after ligation, producing a nick. Cleavage with Vaccinia topoisomerase I opposite to a nick produces a blunt end with covalently attached topoisomerase.

According to another embodiment of the present invention, a nick opposite to a cleavage site of the topoisomerase can be introduced by a restriction enzyme that produces two 3' overhangs that are at least about 8 nucleotides in length, followed by hybridization of the 3' overhangs. An example of restriction enzyme producing 9-base 3' overhangs is TspR I. Other restriction enzymes that produce 3' overhangs at least about 8 nucleotides in length may be known to those skilled in the art and are contemplated herein. The recognition site for such a restriction enzyme is inserted at such a distance from the topoisomerase site that the restriction enzyme cleaves DNA opposite to a cleavage site of the topoisomerase. For example, if restriction enzyme TspR I is used, its recognition site CA(C/G)TG can be placed two nucleotides after the recognition site of a site-specific topoisomerase. After digestion with TspR I, the resulting complementary 3' overhangs are allowed to hybridize, which produces a nick opposite to a cleavage site of the topoisomerase. Treatment with topoisomerase produces a blunt end.

According to the present invention, similar strategies can be employed to produce a 3' overhang with a covalently attached topoisomerase. The 3' overhang can be made if a nick is introduced one or more nucleotides in the 3' direction from a position exactly opposite the topoisomerase cleavage site, followed by treatment with topoisomerase. For example, if a nick is introduced one nucleotide in the 3' direction from a position opposite to the topoisomerase cleavage site, then treatment with topoisomerase produces a 3' T-overhang with a covalently attached topoisomerase.

According to one embodiment of the present invention, a nick 3' from a position opposite to the topoisomerase cleavage site can be created by DNA cleavage with a restriction enzyme, followed by ligation to a double-stranded oligonucleotide adapter. According to another embodiment of the present invention, such a nick can be introduced by DNA digestion with a restriction enzyme that produces two 3' overhangs at least about 8 nucleotides in length, followed by hybridization of the 3' overhangs. In both of these embodiments, the restriction site is positioned so that a restriction enzyme cleaves DNA 3' from a position exactly opposite to the topoisomerase cleavage site. The embodiments differ from the embodiments that describe producing a nick opposite to the topoisomerase cleavage site only in positioning the restriction site relative to the topoisomerase cleavage site.

In another embodiment, the present invention provides a linearized vector which includes an origin of replication, a cohesive circularization end and an insertion end, wherein:

the cohesive circularization end is between about 8 and about 50 nucleotides in length; and the insertion end is either blunt or between 1 and 7 nucleotides in length.

For insertion into this vector, a nucleic acid fragment needs to have a complementary cohesive circularization end that forms either nicks or gaps upon hybridizing with the cohesive circularization end of the vector, and a complementary insertion end that can be ligated to the insertion end of the vector. The cohesive circularization ends of the vector and insert can be made by the methods described above.

In another embodiment, the present invention provides a linearized vector which includes an origin of replication, a cohesive circularization end and an insertion end covalently attached to a site-specific topoisomerase, wherein the cohesive circularization end is between about 8 and about 50 nucleotides in length. The vector end which is covalently attached to a site-specific topoisomerase can also be used as a circularization end, if the corresponding insert end contains a 5' phosphate. In this case the cohesive end can be used as an insertion end. However, circularization mediated by annealing cohesive end is generally preferred to topoisomerase-mediated circularization. The cohesive circularization ends of the vector and insert and the insertion end covalently attached to a site-specific topoisomerase can be prepared by the methods described above.

In another embodiment, the present invention provides a linearized vector which includes an origin of replication, a bacteriophage or virus cos site, and two insertion ends covalently linked to a site-specific topoisomerase. After intermolecular joining mediated by the topoisomerase, the resulting vector-insert concatemers are treated with a terminase of the corresponding bacteriophage or virus, which produces complementary cohesive circularization ends.

The present invention also provides vectors for insertion of nucleic acid fragments by the present topoisomerase-mediated circularization methods. In one embodiment, the present invention provides a linearized vector which includes an origin of replication, an insertion site, and two circularization ends, wherein:

each of the circularization ends is at least about 15 base pairs from the insertion site;

each of the circularization ends is covalently linked through a 3' phosphate to a site specific topoisomerase; and each of the circularization ends contains a 5' phosphate.

The present vector can be cleaved in the insertion site with restriction enzymes and prepared for intermolecular joining by ligation or by a site-specific topoisomerase covalently attached to each of the insertion ends. The circularization ends can not be ligated by either DNA ligase, because they contain 3' phosphates with attached topoisomerase, or by topoisomerase, because they contain 5' phosphates.

In another embodiment, the present invention provides a linearized vector which includes an origin of replication, an insertion site, and two circularization ends, wherein:

each of the circularization ends is at least about 15 base pairs from the insertion site;

one of the circularization ends is covalently linked through a 3' phosphate to a site-specific topoisomerase; and the second circularization end contains a 5' phosphate.

The present vector can be cleaved in the insertion site with restriction enzymes and prepared for intermolecular joining by ligation or by a site-specific topoisomerase covalently attached to each of the insertion ends.

In another embodiment, the present invention provides a linearized vector which includes an origin of replication, a circularization end covalently attached to a site-specific topoisomerase, and an insertion end. If the intermolecular joining is mediated by ligase, the insertion end preferably is dephosphorylated. For topoisomerase-mediated intermolecular joining, the insertion end preferably retains the 5' phosphate.

In another embodiment, the present invention provides one or more compartmentalized kits which includes a first compartment containing a vector of the present invention. Preferably, the vector is linearized. The present invention can also provide another compartment containing a DNA ligase, a further compartment containing a buffer comprising polyethylene glycol of high molecular weight, an additional compartment containing a terminase and/or a still further compartment containing a buffer, for example, a buffer containing a salt.

The present compartmentalized kits include a first compartment containing one of the present vectors. If the intermolecular joining is mediated by ligase, the present kits can provide another compartment containing a DNA ligase, for example, T4 DNA ligase. The present kits can also provide an additional compartment containing a buffer comprising polyethylene glycol of high molecular weight or other water-binding macromolecules that can be used to create conditions of macromolecular crowding during the insertion step. The present kits comprising a present vector containing a bateriophage or virus cos site can provide a further compartment containing a terminase. For circularization performed by reannealing cohesive circularization ends at a high salt concentration, the present kits can provide a still further compartment containing a buffer comprising a salt, for example, ammonium acetate or sodium acetate. For circularization mediated by topoisomerase, the present kits can provide a compartment containing a dephosphorylation enzyme, preferably a thermolabile alkaline phosphatase.

Preferably, the vectors of the present kits are linearized and comprise at least one cohesive or topoisomerase-linked circularization end. If the intermolecular joining is mediated by topoisomerase, the present vectors preferably comprise at least one insertion end covalently linked to topoisomerase. If the intermolecular joining is mediated by ligase, the present kits can contain the present vectors which had been cleaved in their insertion sites by one or two restriction enzymes and the resulting insertion ends dephosphorylated. Alternatively, the present vectors can be provided with uncut insertion sites, giving the users of the kits the choice of restriction enzymes to be used.

The present kits can be designed for specific cloning needs, for example, for construction of cDNA libraries. A cDNA library construction kit can comprise additional compartments containing a reverse transcriptase, dNTPs, and other enzymes and chemicals normally used for the synthesis of first and second cDNA strands. The kit can further include a compartment containing an oligonucleotide comprising deoxythymidine and/or deoxyuracil nucleotides, to be used as a primer for the first strand cDNA synthesis. The kit can also comprise a compartment containing uracil DNA glycosylase that can be used to remove deoxyuracil residues from the 5' end of the first cDNA strand, exposing a 3' oligo(dA) overhang on the second cDNA strand. The linearized vector of this kit preferably comprises a 3' oligo(dT) overhang serving as a cohesive circularization end. Alternatively, a cDNA library construction kit can comprise a DNA polymerase with a proofreading activity that in the absence of dATP can remove all deoxyadenosine residues from the 3' end of the second cDNA strand. The linearized vector of this kit preferably comprises a 5' oligo(dA) overhang serving as a cohesive circularization end.

A cDNA library construction kit can comprise an additional compartment containing an oligoribonucleotide that can be ligated to a 5'-phosphate-containing RNA. The kit can also comprise a compartment containing an oligonucleotide which is identical or at least partially homologous in sequence to the oligoribonucleotide and can be used to prime the second cDNA synthesis. The oligonucleotide can comprise deoxyuracil bases that can be removed by uracil DNA glycosylase after the second strand cDNA synthesis. One or more nucleotides can be missing on the 3' end or 5' end of the oligonucleotide or the 5' end can have additional nucleotides, compared to the oligoribonucleotide. Preferably, the 5' end of the oligonucleotide has at least 8 additional nucleotides that after the second strand cDNA synthesis can form a cohesive circularization end. The kit can also comprise a further compartment containing an RNA ligase, for example, T4 RNA ligase, which can ligate the oligoribonucleotide to a 5' end of RNA. The kit can further comprise a compartment containing a decapping enzyme that can remove the cap structure from the 5' RNA end, for example, Tobacco acid pyrophosphatase. The kit can comprise a still further compartment containing a dephosphorylation enzyme, preferably a thermolabile alkaline phosphatase, to remove 5' phosphates from degraded RNA molecules prior to the RNA treatment with a decapping enzyme.

The following examples further illustrate the invention.

EXAMPLE 1 cDNA Library Construction Using Vectors with Cohesive Circularization Ends and Blunt-Ended Insertion Ends Inverse PCR is performed with Pfu DNA polymerase using pBluescript™ SK+ phagemid (Stratagene) as a vector template and 5' phosphate-containing primers that are complementary to the vector template between the Ampicillin resistance gene (Amp$^r$) and the ColE1 origin. The primer sequences are: 5'-p CGCCCCCCGCGCGTATGAGTAAACTTGGTCTGA-3' (SEQ ID NO: 1); and 5'-p CGCGGGGGGCGCGTATACTTAGATTGATTTAAAAC-3' (SEQ ID NO: 2). Sequences which will lead to formation of the cohesive circularization ends are underlined and are not complementary to the original pBluescript™ SK+ phagemid (Stratagene). After PCR, ligation is performed with T4 DNA ligase, ligation products are transfected into competent *E. coli* cells and colonies are grown. The modified pBluescript™ SK+ is named a pBSSH phagemid, and it contains the following G/C insert between the Amp$^r$ gene and the ColE1 origin:

```
---TATACGCGCCCCCCGCGCGCCCCCCGC
   GCGTAT---                        (SEQ ID NO: 17)

---ATATGCGCGGGGGGCGCGCGGGGGGCG
   CGCATA---                        (SEQ ID NO: 18)
```

The vector sequences are represented above by a dashed line and a recognition site for restriction enzyme BssH II is underlined.

Five μg of pBSSH phagemid are digested with 10 units of restriction enzyme BssH II for 2 hours at 50° C. in 100 μl of 1×BssH II buffer. After digestion, dATP and dTTP are added to 0.5 mM each and the mixture is incubated with 15 units of T4 DNA polymerase and 2 units of Shrimp alkaline phosphatase for 30 min. at 37° C. T4 DNA Polymerase removes all G and C nucleotides from the DNA ends, producing a modified pBSSH phagemid, shown below as a linearized vector with most vector sequences represented by a dashed line, and the sequence of the cohesive circularization ends as follows:

```
5'-CGCGCCCCCCGCGCGTAT------TATA-3'   (SEQ ID NO: 19)

3'-ATA------ATATGCGCGGGGGGCGCGC-5'   (SEQ ID NO: 20)
```

The products are heated to 70° C. for 15 min, treated with phenol-chloroform and precipitated with ethanol. The pellet is dissolved in 0.5 ml TE, aliquoted as desired and placed to −20° C. freezer. The resulting stock of phagemid with cohesive circularization ends corresponds to the vector illustrated in step 1 of FIG. 1.

To make cDNA, first strand synthesis on poly(A)+ RNA is primed with a 5' phosphate-containing oligonucleotide 5'-pTTTTTTTTTTTTTTTTTTTTTTTT-3' (SEQ ID NO: 3) at 48° C. using SuperScripts™ II reverse transcriptase (Life Technologies), according to manufacturer's recommendations. The second strand cDNA synthesis is performed using RNase H, DNA Polymerase I, and *E. coli* DNA Ligase. After the synthesis, both ends of double-stranded cDNA contain 5' phosphates.

100 ng of the modified pBSSH phagemid with cohesive circularization ends are digested for 1 hour in 20 μl of 1×EcoR V buffer with 1 unit of EcoR V in the presence of 0.2 units of Shrimp Alkaline Phosphatase. The products are heated to 70° C. for 15 min, treated with phenol-chloroform and precipitated with ethanol. The product corresponds to the vector cut into two parts as depicted in step 2 of FIG. 1.

Ligation of 100 ng of the phagemid and 2 ng of the cDNA is performed at 20° C. for 1 hour in 20 μl of 1×T4 DNA Ligase buffer containing 15% PEG 8,000 and 2 Weiss units of T4 DNA Ligase. The products of this reaction are depicted in step 3 of FIG. 1.

Ligation products are pelleted in a microcentrifuge, washed in 70% ethanol and dissolved in 300 μl of Melting Buffer (10 mM Tris-acetate, 5 mM EDTA, 2 mM dithiothreitol, pH 8.0 at 25° C.). Melting is performed at 65° C. for 5 min., resulting in the separation of a linear vector-cDNA monomer from a vector-cDNA-vector concatemer, which is illustrated in step 4 of FIG. 1.

Circularization is initiated by the addition of 100 μl of 10 M ammonium acetate, which increases the melting temperature of the cohesive circularization ends. After incubation at 72° C. for 6 hours, almost all vector-cDNA monomers, regardless of their length, become circularized (step 5 of FIG. 1). Circularization products are mixed with 10 μg of yeast tRNA and precipitated with 2.5 volumes of ethanol (1 ml). The pellet is dissolved in 10 μTE, out of which 5 μl are electroporated into electro-competent *E. coli* cells that have $10^{10}$ colonies/μg transformation efficiency.

EXAMPLE 2 cDNA Library Construction Using Vectors with Cohesive Circulaization Ends and Blunt-Ended Insertion Ends Linked to Topoisomerase The pBSSH phagemid from Example 1 contains 10 recognition sites for restriction enzyme TspR I (CA(G/C)TG). The TspR I sites are eliminated by several rounds of inverse PCR with Pfu DNA polymerase, introducing silent mutations that do not change amino acid sequence of the corresponding proteins. After elimination of all TspR I sites in pBSSH, inverse PCR with Pfu DNA polymerase is performed with 5' phosphate-containing primers that are complementary to the multiple cloning site of pBSSH. The primer sequences are:

```
5'-pGTGGGAAGGGCTGCAGGAATTCGA-3'    (SEQ ID NO: 4);
``` and

```
5'-pTGCCAAGGGGGATCCACTAGTTC-3'     (SEQ ID NO: 5).
```

Additional sequences, which are not complementary to pBSSH, are underlined. The phagemid is circularized by ligation with T4 DNA ligase, transfected into competent *E. coli* cells and colonies are grown. The Sma I site of the modified pBSSH phagemid is interrupted by insertion of an oligonucleotide, which does not change the reading frame at lacZ gene, to yield the following:

```
---CCCTTGGCAGTGGGAAGGG---          (SEQ ID NO: 21)

---GGGGAACCGTCACCCTTC---           (SEQ ID NO: 22)
```

The vector sequences are represented above by a dashed line, the recognition site of restriction enzyme TspR I is underlined, and two inverted recognition sites of Vaccinia topoisomerase I are double-underlined. The modified pBSSH phagemid is named pBSvac2-blunt.

Two μg of pBSvac2-blunt phagemid are digested with 4 units of restriction enzyme BssH II for 2 hours at 50° C. in 40 μl of 1×BssH II buffer. After digestion, dATP and dTTP are added to 0.5 mM each and the mixture is incubated with 6 units of T4 DNA polymerase for 30 min. at 37° C. The products are treated with phenol-chloroform and precipitated with ethanol. This corresponds to the vector illustrated in step 1 of FIG. 2.

The pBSvac2-blunt phagemid with cohesive circularization ends is digested with 8 units of restriction enzyme TspR I (New England Biolabs) for 2 hours at 65° C. in 30 μl of 1×NEBuffer 4+BSA. The products are treated with phenol-chloroform and precipitated with ethanol. After digestion, the pBSvac2-blunt phagemid consists of two parts each of which contains two cohesive ends: a 9-base 3' overhang and a 14-base 5' overhang.

```
5'-pCGCGCCCCCGCGCGTAT---CCCTTGGCAGT
   GGG-3'                           (SEQ ID NO: 23)

3'-ATA---GGGAAp-5'
``` and

```
5'-pAAGGG---TATA-3'                 (SEQ ID NO: 25)

3'-CCGTCACCCTTCCC---ATATGCGCGGGGGCG
   CGp-5'                           (SEQ ID NO: 26)
```

The pellet is dissolved in 5 μl of 1×Vaccinia topoisomerase I buffer (50 mM Tris-acetate, 100 mM NaCl, 2.5 mM MgCl₂, 0.1 mM EDTA, pH 7.5) and incubated at room temperature for 1 hour, to allow the cohesive ends to anneal to each other. The resulting concatemers of phagemid parts with hybridized cohesive ends are treated with 20 units of Vaccinia topoisomerase I (Epicentre Technologies) for 2 hours at 30° C. in 20 μl of 1×Vaccinia topoisomerase I buffer. Topoisomerase cleavage after the last thymidine of its recognition site, opposite to a nick produced by hybridized 9-base 3' overhangs, produces a blunt end. Topoisomerase forms a covalent bond with the 3' phosphate of the last thymidine, whereas the 9-base 3' overhang dissociates from the topoisomerase-DNA complex. The phagemid with two hybridized cohesive circularization ends and two blunt-ended topoisomerase-linked insertion ends corresponds to the vector cut into two parts as depicted in step 2 of FIG. 2. The phagemid is also depicted below with most vector parts represented by dashed lines:

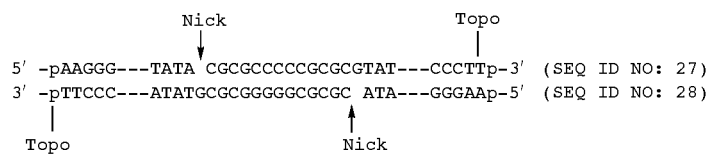

The phagemid with attached topoisomerase is purified using StrataPrep™ PCR Purification Kit (Stratagene) according to manufacturer's recommendations.

Poly(A)+ RNA is dephosphorylated with Shrimp alkaline phosphatase and heated to 70° C. for 15 min. to inactivate phosphatase. RNA is treated with Tobacco acid pyrophosphatase (Epicentre Technologies) that removes the cap structure from the 5' RNA end and replaces it with a 5' phosphate. An oligoribonucleotide 5'-rGCCCGGGCGGCCGC-3' (SEQ ID No: 6) is ligated to the 5' RNA end with T4 RNA ligase. The first strand cDNA synthesis on the RNA with ligated oligoribonucleotide is primed with an oligonucleotide

5'-TTTTTTTTTTTTTTTTTTTTTTTTT-3'    (SEQ ID NO: 3)

at 48° C. using SuperScript™ II reverse transcriptase (Life Technologies). RNA is hydrolyzed with alkali and the second strand cDNA synthesis is performed at 60° C. using Pfu DNA polymerase and an oligonucleotide 5'-GCCCGGGCGGCCGC-3' (SEQ ID NO: 7) that is identical in sequence to the oligoribonucleotide SEQ ID NO: 6 but contains deoxyribonucleotides. After the synthesis, both cDNA ends are dephosphorylated.

100 ng of the pBSvac2-blunt phagemid with attached topoisomerase and hybridized cohesive circularization ends are mixed with 2 ng of the dephosphorylated cDNA in 20 μl of 1×Vaccinia topoisomerase I buffer containing 15% PEG 8,000 and incubated at 25° C. for 30 min. The products of this reaction are depicted in step 3 of FIG. 2. After incubation, MgCl₂ is added to 10 mM and the products are pelleted in a microcentrifuge. The following steps (melting, circularization, precipitation and electroporation) are identical to those of the Example 1.

EXAMPLE 3 cDNA Library Construction Using a Vector with a Cohesive Circularization End and a Blunt-Ended Insertion End Ten μg of pBluescript™ SK+ phagemid (Stratagene) are digested for 2 hours with 30 units of restriction enzyme EcoR V and 20 units of restriction enzyme Spe I in the presence of 4 units of Shrimp alkaline phosphatase in 100 ml of 1×EcoR V buffer, heated to 70° C. for 15 min., treated with phenol-chloroform and ethanol precipitated. A 5' phosphate-containing oligonucleotide with the sequence:

5'-pCTAGTTTTTTTTTTTTTTTTTTTTTTTTT-3'    (SEQ ID NO: 8)

is ligated to the sticky end of the pBluescript™ SK+ vector provided by the Spe I digestion. Five hundred pmole of the oligonucleotide are used for ligation in 30 μl of 1× of T4 DNA Ligase buffer containing 15% PEG 8,000 and 20 Weiss units of T4 DNA Ligase. Ligation products are spun in a microcentrifuge, which eliminates the excess free oligonucleotide. The pellet is dissolved in 0.5 ml TE. This modified pBluescript™ SK+ phagemid is named pBST24-blunt. This vector corresponds to the vector illustrated in step 1 of FIG. 3, and is depicted below with vector sequences represented by dashed lines and the sequences of the ends provided.

5'-ATC----ACTAGTTTTTTTTTTTTTTTTTTTT
   TTT-3'    (SEQ ID NO: 29)

3'-TAG----TGATC-5'    (SEQ ID NO:30)

First strand cDNA synthesis on a poly(A)+ RNA template is primed with an oligonucleotide 5'-TTUTTUTTUTTUTTUTTUTTUTTU-3' (SEQ ID NO: 9) at 48° C. using SuperScript™ II reverse transcriptase (Life Technologies). The second strand cDNA synthesis is performed using RNase H, DNA Polymerase I, and E. coli DNA Ligase. After the synthesis, the double-stranded cDNA is treated with uracil DNA glycosylase that removes deoxyuracil residues from the 5' end of the first cDNA strand, disrupting base-pairing and exposing 3' oligo(dA) overhang on the second cDNA strand. The 5' end of the second cDNA strand contains phosphate.

Ligation of 100 ng of the pBST24-blunt phagemid and 2 ng of the cDNA with the 3' oligo(dA) overhang is performed at 20° C. for 1 hour in 20 μl of 1×T4 DNA Ligase buffer containing 15% PEG 8,000 and 2 Weiss units of T4 DNA Ligase. The products of this reaction are depicted in step 2 of FIG. 3.

The ligation products are pelleted in a microcentrifuge, washed in 70% ethanol and dissolved in 300 μl of Melting buffer. The melting, circularization, precipitation and electroporation steps are as described in Example 1.

EXAMPLE 4 cDNA Library Construction Using Vectors with a Cohesive Circularization End and a Blunt-Ended Topoisomerase-Linked Insertion End Inverse PCR with pBluescript™ SK+ phagemid (Stratagene) and Pfu DNA polymerase is performed with 5' phosphate-containing primers that are complementary to the multiple cloning site of pBluescript™ SK+ and contain additional 5' sequences. The primer sequences are:

5'-pTCTTCCTTATCGATACCGTCGAC-3'    (SEQ ID NO: 10)

and

5'-pCGCCCTTGATATCGAATTCCTGC-3'    (SEQ ID NO: 11).

The phagemid is circularized by ligation with T4 DNA ligase and transfected into competent *E. coil* cells. The Hind III site of the modified pBluescript™ SK+ phagemid is interrupted by a sequence that does not change the reading frame of lacZ gene:

---<u>AAGGGCGTCTTC</u>---    (SEQ ID NO: 31)

---TTCCCGCAGAAG---    (SEQ ID NO: 32)

where the vector sequences are represented by a dashed line, the recognition site of restriction enzyme Bbs I is underlined, and a recognition site of Vaccinia topoisomerase I is double-underlined. The modified pBluescript™ SK+ phagemid is designated as pBSvac1-blunt.

Two μg of pBSvac1-blunt phagemid are digested with 3 units of restriction enzyme Bbs I (New England Biolabs) and 3 units of restriction enzyme Not I. The products are heated to 70° C. for 15 min, treated with phenol-chloroforrn and precipitated with ethanol.

5'-pAAGGGCGTCTTC------C-3'    (SEQ ID NO: 33)

3'-CGCAGAAG------GCCGGp-5'    (SEQ ID NO: 34)

The sticky end left by the Not I digestion of the phagemid is ligated to an oligonucleotide 5'-pGGCCTTTTTTTTTTTTTTTTTTTTTTTT-3' (SEQ ID NO: 12), whereas the sticky end left by the Bbs I digestion is ligated to a double-stranded oligonucleotide adapter formed by the annealing of a 5' phosphate-containing oligonucleotide 5'-pCCTTCGCACGCTCGGCAC-3' (SEQ ID NO: 13) to a complementary 3' phosphate-containing oligonucleotide 5'-GTGCCGAGCGTGCGp-3' (SEQ ID NO: 14). 100 pmole of each oligonucleotide are used for ligation in 30 μl of 1× of T4 DNA ligase buffer containing 15% PEG 8,000 and 10 Weiss units of T4 DNA ligase. Ligation is performed at 20° C. for 4 hours, after which the ligation products are pelleted in a microcentrifuge.

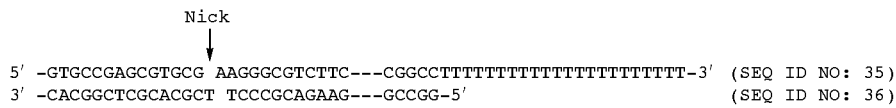

```
                 Nick
                  ↓
5' -GTGCCGAGCGTGCG AAGGGCGTCTTC---CGGCCTTTTTTTTTTTTTTTTTTTTTT-3'  (SEQ ID NO: 35)
3' -CACGGCTCGACGCT TCCCGCAGAAG---GCCGG-5'                         (SEQ ID NO: 36)
```

The pellet is dissolved in 20 μl of 1×Vaccinia topoisomerase I buffer and incubated with 20 units of Vaccinia topoisomerase I (Epicentre Technologies) for 2 hours at 37° C. Topoisomerase cleavage after the last thymidine of its recognition site, across from a nick resulting from hybridization of the oligonucleotide SEQ ID NO: 9 to the complementary sequence, produces a blunt end with topoisomerase covalently linked to the 3' phosphate:

end is designated as pBST24vac. This corresponds to the vector depicted in step 1 of FIG. 4. The phagemid is purified using StrataPrep™ PCR Purification Kit (Stratagene).

Poly(A)+ RNA is treated as in Example 2 to ligate the oligoribonucleotide 5'-rGCCCGGGCGGCCGC-3' (SEQ ID NO:6) to the 5' RNA end. The first strand cDNA synthesis on poly(A)+ RNA is primed with an oligonucleotide 5'-TTUTTUTTUTTUTTUTTUTTUTTU-3' (SEQ ID NO: 9) at 48° C. using SuperScript™ II reverse transcriptase (Life Technologies). RNA is hydrolyzed with alkali and the second strand cDNA synthesis is performed using Pfu DNA polymerase and the oligonucleotide 5'-GCCCGGGCGGCCGC-3' (SEQ ID NO: 7). The cDNA is treated with uracil DNA glycosylase that removes uracil residues, disrupting base-pairing and exposing 3' oligo(dA)$_{24}$ overhang.

One hundred ng of the pBST24vac phagemid with attached topoisomerase are mixed with 2 ng of the cDNA in 20 μl of 1×Vaccinia topoisomerase I buffer containing 15% PEG 8,000 and incubated at 25° C. for 30 min. After incubation, MgCl$_2$ is added to 10 mM and the products are pelleted in a microcentrifuge. The resulting vector-insert-vector construct with two hybridized cohesive circularization ends is illustrated in step 2 of FIG. 4. The following steps (melting, circularization, precipitation and electroporation) are identical to those of the Example 1.

EXAMPLE 5 cDNA Library Construction Using Vectors with Topoisomerase-Linked Circularization Ends and Topoisomerase-Linked Insertion Ends Inverse PCR with the pBSvac2-blunt phagemid from Example 2 is performed with Pfu DNA polymerase and 5' phosphate-containing primers that are complementary to the region between the Ampicillin resistance gene (Amp)$^r$ and the ColE1 origin. The primer sequences are:

5'-p CGTCGCGGAAGGGTATGAGTAAACTTGGTCTGA-3' (SEQ ID NO: 15) and 5'-p TCCGCGAAGGGTATACTTTAGATTGATTTAAAAC-3' (SEQ ID NO: 16). Additional sequences, which are not complementary to the pBSvac2-blunt phagemid, are underlined. After PCR, ligation is performed with T4 DNA ligase, ligation products are transfected into competent *E. coli* cells and colonies are grown. The modified pBSvac2-blunt phagemid is named pBSvac4-blunt. It contains the following insert between Amp$^r$ gene and ColE1 origin:

```
5' -pAAGGGCGTCTTC---GGCCTTTTTTTTTTTTTTTTTTTTTT-3'  (SEQ ID NO: 37)
3' -pTTCCCGCAGAAG---CCGG-5'                        (SEQ ID NO: 38)
  |
  Topo
```

The phagemid with an oligo(dT)$_{24}$ cohesive circularization end and a blunt-ended topoisomerase-linked insertion

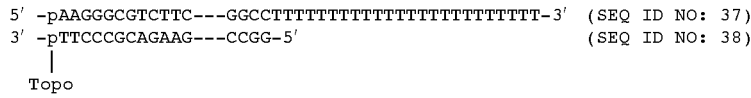

---CCCTTCGCG<u>GACGTCGC</u>GGAAGGG---    (SEQ ID NO: 39)

---GGGAAGCGCCTGCAGCGCCTTCCC---    (SEQ ID NO: 40)

where the recognition site of restriction enzyme Aat II is underlined, and two inverted recognition sites of Vaccinia topoisomerase I are double-underlined.

Two µg of the pBSvac4-blunt phagemid are digested with 5 units of restriction enzyme Aat II for 2 hours at 37° C. in 30 µl of 1×NEBuffer 4+BSA, followed by the addition of 4 units of restriction enzyme TspR I (New England Biolabs) and incubation for 2 hours at 65° C. The products are treated with phenol-chloroform and precipitated with ethanol. After digestion, the pBSvac4-blunt phagemid consists of two parts:

5'-pCGCGGAAGGG---<u>CCCTT</u>GGCAGT
    GGG-3' (SEQ ID NO: 41)

3'-TGCAGCGCCTTCCC---GGGAAp-5' (SEQ ID NO: 42)

and

5'-p<u>AAGGG</u>---CCCTTCGAGGAGT-3' (SEQ ID NO: 43)

3'-CCGTCACCCTTCCC---GGGAAGCGCCp-5' (SEQ ID NO: 44)

The pellet is dissolved in 5 µl of 1×Vaccinia topoisomerase I buffer and incubated at room temperature for 1 hour, to reanneal the 9-base 3' overhangs produced by TspRI digestion. After the incubation, 15 µl of 1×Vaccinia topoisomerase I buffer are added and the phagemid is treated with 20 units of Vaccinia topoisomerase I (Epicentre Technologies) for 2 hours at 30° C. The product corresponds to the vector cut into two parts with four attached topoisomerase molecules as depicted in step 1 of FIG. 6. The two vector parts are also depicted below, with vector sequences represented by dashed line, and the sequences of the ends provided:

```
                    Topo
                     |
    5' -pCGCGGAAGGG---CCCTTp-3'    (SEQ ID NO: 45)
        3' -pTTCCC---GGGAAp-5'    (SEQ ID NO: 46)
                |
               Topo
               and
               Topo
                |
    5' -pAAGGG---CCCTTp-3'         (SEQ ID NO: 47)
    3' -pTTCCC---GGGAAGCGCCp-5'    (SEQ ID NO: 48)
                |
               Topo
``` cDNA is synthesized as in Example 2. 100 ng of the pBSvac4-blunt phagemid with attached topoisomerase are mixed with 2 ng of the dephosphorylated cDNA in 20 µl of 1×Vaccinia topoisomerase I buffer containing 15% PEG 8,000 and incubated at 25° C. for 30 min. After incubation, MgCl$_2$ is added to provide a concentration of 10 mM and the products are spun in a microcentrifuge. The resulting vector-insert monomer with topoisomerase attached to vector circularization ends is illustrated in step 2 of FIG. 6.

The pellet is dissolved in 400 µl of 1×Vaccinia topoisomerase I buffer and incubated with 40 units of Shrimp alkaline phosphatase for 18 hours at 37° C. After the removal of 5' phosphates by the alkaline phosphatase, topoisomerase joins the circularization ends in an intramolecular reaction. The products are heated to 70° C. for 15 min. and ethanol precipitated with 10 µg of yeast tRNA as carrier. The pellet is dissolved in 10 µl TE and 5 µl are electroporated into electro-competent E. Coli cells with $10^{10}$ colonies/µg transformation efficiency.

EXAMPLE 6 cDNA Library Construction Using Vectors with Blunt Ends Linked to Topoisoinerase Two µg of the pBSvac2-blunt phagemid from Example 2 are digested with 4 units of restriction enzyme TspR I (New England Biolabs) for 2 hours at 65° C. in 30 µl of 1×NEBuffer 4+BSA, followed by treatment with phenol-chloroform and precipitation with ethanol. The digested phagemid is incubated for 1 hour at room temperature to reanneal the 9-base 3' overhangs produced by TspRI digestion and then treated with 20 units of Vaccinia topoisomerase I (Epicentre Technologies) for 2 hours at 30° C. in 20 µl of 1×Vaccinia topoisomerase I buffer. The phagemid is purified using StrataPrep™ PCR Purification Kit (Stratagene). This corresponds to the blunt-ended vector with attached topoisomerase which is depicted below and in step 1 of FIG. 7. Vector sequences are depicted as dashed lines and the sequences of the ends are provided.

```
               Topo
                |
    5' -pAAGGG---CCCTTp-3'    (SEQ ID NO: 49)
    3' -pTTCCC---GGGAAp-5'    (SEQ ID NO: 50)
                |
               Topo
```

The first strand cDNA synthesis on poly(A)+ RNA is primed with an oligonucleotide 5'-TTTTTTTTTTTTTTTTTTTTTTTT-3' (SEQ ID NO: 3) at 48° C. using SuperScript™ II reverse transcriptase (Life Technologies). The second strand cDNA synthesis is performed using RNase H, DNA Polymerase I, and E. coli DNA Ligase. After the synthesis, the 5' phosphate-containing end of the second cDNA strand serves as a circularization end, whereas the dephosphorylated 5' end of the first cDNA strand serves as an insertion end.

100 ng of the linearized pBSvac2-blunt phagemid with attached topoisomerase are mixed with 2 ng of the cDNA in 20 µl of 1×Vaccinia topoisomerase I buffer containing 15% PEG 8,000 and incubated at 25° C. for 30 min. Only the 5' end of the first cDNA strand which is dephosphorylated, can be joined by topoisomerase to a vector's end. The phosphate on the 5' end of the second cDNA strand blocks the joining by topoisomerase. The products of this reaction are depicted in step 2 of FIG. 7. After the addition of MgCl$_2$ to 10 mM, the products are pelleted in a microcentrifuge. The following steps (incubation with Shrimp alkaline phosphatase, precipitation and electroporation) are identical to those of the Example 5.

What is claimed is:

1. A method for inserting a nucleic acid fragment into a circular vector, which comprises:

(a) stably joining an insertion end of a nucleic acid fragment with an insertion end of a linearized vector at a first nucleic acid concentration under conditions favoring intermolecular joining, to form a linear vector-insert concatemer;

(b) melting hybridized cohesive circularization ends in said vector-insert concatemer to form a linear vector-insert monomer having single-stranded cohesive circularization ends; and (c) reannealing said single-stranded cohesive circularization ends at a second nucleic acid concentration under conditions favoring circularization to form a circularized vector containing a nucleic acid insert;

wherein said second nucleic acid concentration is more dilute than said first nucleic acid concentration and wherein said cohesive circularization ends are between about 8 and about 50 nucleotides in length.

2. The method of claim 1 wherein said linearized vector comprises two vector parts, each vector part having:
   (i) an insertion end; and
   (ii) a cohesive circularization end which can hybridize to a complementary cohesive circularization end of the second vector part.

3. The method of claim 1 wherein said linearized vector comprises an insertion end and a cohesive circularization end and wherein said nucleic acid fragment comprises:
   (i) an insertion end that is complementary to said insertion end of said linearized vector; and
   (ii) a cohesive circularization end that is complementary to said cohesive circularization end of said linearized vector.

4. The method of claim 1 wherein:
said vector has a recognition site for an enzyme or enzyme complex which creates a first nick in one strand which is about 8 to about 50 nucleotides from a second nick in the other strand;
after said joining, said method further comprises nicking said vector-insert concatemer with said enzyme or enzyme complex to produce cohesive circularization ends;

said nicking is not accompanied by packaging into phage particles; and said recognition site is at least about 15 nucleotides in length.

5. The method of claim 1 further comprising the step of forming said cohesive circularization ends by the use of an enzyme or enzyme complex which creates a first nick in one strand which is about 8 to about 50 nucleotides from a second nick in the other strand.

6. The method of claim 1 further comprising the step of forming said cohesive circularization ends by the use of a terminase of a bacteriophage or virus, but wherein said vector-insert monomer is not packaged into a phage particle.

7. The method of claim 1 further comprising the step of forming said cohesive circularization ends by ligation of oligonucleotide adapters, tailing with terminal transferase, digestion with an exonuclease, digestion with a DNA polymerase possessing proofreading activity, or removal of uracil residues by uracil DNA glycosylase after polymerase chain reaction using dUMP-containing primers.

8. The method of claim 1 wherein said cohesive circularization ends comprise nucleotide analogs.

9. The method of claim 1 wherein said reannealing is performed at a salt concentration which is higher than the salt concentration used for said melting.

10. The method of claim 1 wherein said reannealing is performed at a salt concentration which is between about 100 mM and about 7.5 M.

11. The method of claim 1 wherein said reannealing is performed to about 50° C. to about 85° C.

12. A method for inserting a nucleic acid fragment into a circular vector, which comprises:
(a) stably joining an insertion end of a nucleic acid fragment with an insertion end of a linearized vector at a first nucleic acid concentration under conditions favoring intermolecular joining, to form a linear vector-insert construct with complementary circularization ends, wherein one or both circularization ends of said vector-insert construct (1) are attached to an enzyme or enzyme complex capable of covalently joining DNA ends, and (2) are blocked from covalent joining;
(b) unblocking said circularization ends of said vector-insert construct; and
(c) joining said circularization ends of said insert-vector construct at a second nucleic acid concentration in an intramolecular reaction mediated by said enzyme or enzyme complex under conditions favoring circularization, to form a circularized vector containing a nucleic acid insert;
wherein said second nucleic acid concentration is more dilute than said first nucleic acid concentration.

13. The method of claim 12 wherein:
said enzyme or enzyme complex is a site-specific topoisomerase that is covalently linked through a 3' phosphate to a circularization end;
one or both circularization ends are blocked from covalent joining by 5' phosphates;
said unblocking is achieved by removing said 5' phosphates from said circularization ends; and
said site-specific topoisomerase does not substantially covalently join said circularization ends of said vector-insert construct until the 5'-phosphates are removed from said circularization ends.

14. The method of claim 12 wherein said linearized vector comprises two vector parts, each vector part having an insertion end and a circularization end, and wherein one or both of said circularization ends (1) are attached to an enzyme or enzyme complex capable of covalently joining DNA ends, and (2) are blocked from covalent joining.

15. The method of claim 12 wherein:
said linearized vector comprises an insertion end and a circularization end;
said nucleic acid fragment comprises an insertion end that is complementary to said insertion end of said linearized vector and a cohesive circularization end that is complementary to said cohesive circularization end of said linearized vector;
either said circularization end or said complementary circularization end is attached to an enzyme or enzyme complex capable of covalent joining DNA ends; and
both said circularization end and said complementary circularization end are blocked from covalent joining.

16. The method of claim 12 wherein said joining is mediated by annealing a cohesive insertion end of said linearized vector to a complementary cohesive insertion end of said nucleic acid fragment, wherein each of said cohesive insertion ends is between about 8 to about 50 nucleotides in length.

17. The method of claim 1 or 12 wherein said joining is mediated by ligase and wherein ligase does not substantially covalently join said circularization ends.

18. The method of claim 1 or 12 wherein said joining is mediated by a site-specific topoisomerase covalently linked to said insertion end of said linearized vector or said insertion end of said nucleic acid fragment.

19. The method of claim 1 or 12 wherein said joining is mediated by Vaccinia virus topoisomerase I or a Vaccinia virus topoisomerase I fusion protein covalently linked to said insertion end of said linearized vector or said insertion end of said nucleic acid fragment.

20. The method of claim 1 or 12 wherein at least one of said insertion ends or at least one of said circularization ends comprises a blunt end covalently linked to a site-specific topoisomerase and wherein said method further comprises preparing said blunt end by:
(a) creating a nick in a DNA strand that is exactly opposite to a topoisomerase cleavage site in the complementary DNA strand; and
(b) cleaving with said site-specific topoisomerase at said topoisomerase cleavage site to produce a blunt end.

21. The method of claim 1 or 12 wherein at least one of said insertion ends or at least one of said circularization ends comprises a 3' overhang covalently linked to a site-specific topoisomerase and wherein said method further comprises preparing said 3' overhang by:
(a) creating a nick in a DNA strand that is located one or more nucleotides in the 3' direction from a position exactly opposite to a topoisomerase cleavage site in the complementary DNA strand; and
(b) cleaving with said site-specific topoisomerase at said topoisomerase cleavage site to produce a 3' overhang.

22. The method of claim 1 or 12 wherein said nucleic acid fragment is selected from the group consisting of eukaryotic, prokaryotic, viral, and bacteriophage genomic DNA, cDNA, cDNA:RNA hybrid, polymerase chain reaction product and vector DNA.

23. The method of claim 1 or 12 wherein said nucleic acid fragment is present at $10^{-21}$ to $10^{-14}$ mole.

24. The method of claim 1 or 12 wherein said first nucleic acid concentration comprises a molar ratio of linearized vector to nucleic acid fragment which is about 10:1 to about 100,000,000:1.

25. The method of claim 1 or 12 wherein said conditions favoring intermolecular joining are macromolecular crowding conditions.

26. The method of claim 1 or 12 wherein said second nucleic acid concentration is less than one tenth of said first nucleic acid concentration.

27. The method of claim 1 or 12 wherein the efficiency of insertion of said nucleic acid fragment into said circular vector is at least about 95%.

28. The method of claim 1 or 12 wherein the efficiency of forming a circularized vector containing only one nucleic acid insert is at least about 95%.

29. The method of claim 1 or 12 wherein the efficiency of forming a circularized vector containing an insert is substantially the same over a range of insert sizes varying from about 20 base pairs to about 20,000 base pairs.

30. The method of claim 1 or 12 wherein said nucleic acid fragment is between 20 base pairs and 100,000 base pairs in length.

31. A linearized vector comprising an origin of replication, two blunt or sticky ends, and two cohesive ends, wherein:

said cohesive ends are between about 8 and about 50 nucleotides in length;

each of said blunt or sticky ends is covalently linked to a site-specific topoisomerase; and each of said blunt or sticky ends has a 5'-phosphate.

32. A linearized vector comprising an origin of replication, a blunt or sticky end covalently linked to a site-specific topoisomerase, and a cohesive end, wherein said cohesive end is between about 8 and about 50 nucleotides in length.

33. A kit comprising a first compartment containing the linearized vector of claim 31 or 32.

34. The kit of claim 33 which further comprises:

a second compartment containing a buffer comprising polyethylene glycol of high molecular weight; and a third compartment containing a buffer comprising a salt.

35. A linearized vector comprising an origin of replication, two insertion ends, and two circularization ends wherein:

each of said circularization ends is located at least 15 base pairs from each of said insertion ends;

each of said insertion ends is covalently linked to a site-specific topoisomerase;

one or both of said circularization ends are covalently linked to a site-specific topoisomerase; and each of said insertion ends and each of said circularization ends has a 5'-phosphate.

36. A kit comprising a first compartment containing the linearized vector of claim 35.

37. A linearized vector comprising an origin of replication, a bacteriophage or virus cos site, and two insertion ends covalently linked to a site-specific topoisomerase.

38. A kit comprising a first compartment containing the linearized vector of claim 37.

39. The kit of claim 38 which further comprises:

a second compartment containing a buffer comprising high molecular weight polyethylene glycol;

a third compartment containing a terminase; and a fourth compartment containing a buffer comprising a salt.

* * * * *

SEQUENCE LISTING

<160> NUMBER OF SEQ ID NOS: 50

<210> SEQ ID NO 1
<211> LENGTH: 33
<212> TYPE: DNA
<213> ORGANISM: Artificial Sequence
<220> FEATURE:
<223> OTHER INFORMATION: Cloning Vector

<400> SEQUENCE: 1
cgccccccgc gcgtatgagt aaacttggtc tga        33

<210> SEQ ID NO 2
<211> LENGTH: 36
<212> TYPE: DNA
<213> ORGANISM: Artificial Sequence
<220> FEATURE:
<223> OTHER INFORMATION: Cloning Vector

<400> SEQUENCE: 2
cgcggggggc gcgtatactt tagattgatt taaaac        36

<210> SEQ ID NO 3
<211> LENGTH: 24
<212> TYPE: DNA
<213> ORGANISM: Artificial Sequence
<220> FEATURE:
<223> OTHER INFORMATION: Cloning Vector

<400> SEQUENCE: 3
tttttttttt tttttttttt tttt        24

<210> SEQ ID NO 4
<211> LENGTH: 24
<212> TYPE: DNA
<213> ORGANISM: Artificial Sequence
<220> FEATURE:
<223> OTHER INFORMATION: Cloning Vector

<400> SEQUENCE: 4
gtgggaaggg ctgcaggaat tcga        24

<210> SEQ ID NO 5
<211> LENGTH: 23
<212> TYPE: DNA
<213> ORGANISM: Artificial Sequence
<220> FEATURE:
<223> OTHER INFORMATION: Cloning Vector

<400> SEQUENCE: 5
tgccaagggg gatccactag ttc        23

<210> SEQ ID NO 6
<211> LENGTH: 14
<212> TYPE: DNA
<213> ORGANISM: Artificial Sequence
<220> FEATURE:
<223> OTHER INFORMATION: Cloning Vector

<400> SEQUENCE: 6
gcccgggcgg ccgc        14

<210> SEQ ID NO 7
<211> LENGTH: 14

```
<212> TYPE: DNA
<213> ORGANISM: Artificial Sequence
<220> FEATURE:
<223> OTHER INFORMATION: Cloning Vector

<400> SEQUENCE: 7
gcccgggcgg ccgc                                                      14

<210> SEQ ID NO 8
<211> LENGTH: 28
<212> TYPE: DNA
<213> ORGANISM: Artificial Sequence
<220> FEATURE:
<223> OTHER INFORMATION: Cloning Vector

<400> SEQUENCE: 8
ctagtttttt tttttttttt tttttttt                                       28

<210> SEQ ID NO 9
<211> LENGTH: 25
<212> TYPE: DNA
<213> ORGANISM: Artificial Sequence
<220> FEATURE:
<223> OTHER INFORMATION: Cloning Vector

<400> SEQUENCE: 9
rttuttuttu ttuttuttut tuttu                                          25

<210> SEQ ID NO 10
<211> LENGTH: 23
<212> TYPE: DNA
<213> ORGANISM: Artificial Sequence
<220> FEATURE:
<223> OTHER INFORMATION: Cloning Vector

<400> SEQUENCE: 10
tcttccttat cgataccgtc gac                                            23

<210> SEQ ID NO 11
<211> LENGTH: 23
<212> TYPE: DNA
<213> ORGANISM: Artificial Sequence
<220> FEATURE:
<223> OTHER INFORMATION: Cloning Vector

<400> SEQUENCE: 11
cgcccttgat atcgaattcc tgc                                            23

<210> SEQ ID NO 12
<211> LENGTH: 28
<212> TYPE: DNA
<213> ORGANISM: Artificial Sequence
<220> FEATURE:
<223> OTHER INFORMATION: Cloning Vector

<400> SEQUENCE: 12 ggccttttttt tttttttttt tttttttt                                      28

<210> SEQ ID NO 13
<211> LENGTH: 18
<212> TYPE: DNA
<213> ORGANISM: Artificial Sequence
<220> FEATURE:
<223> OTHER INFORMATION: Cloning Vector

<400> SEQUENCE: 13
```
ccttcgcacg ctcggcac                                          18

<210> SEQ ID NO 14
<211> LENGTH: 14
<212> TYPE: DNA
<213> ORGANISM: Artificial Sequence
<220> FEATURE:
<223> OTHER INFORMATION: Cloning Vector

<400> SEQUENCE: 14
gtgccgagcg tgcg                                              14

<210> SEQ ID NO 15
<211> LENGTH: 33
<212> TYPE: DNA
<213> ORGANISM: Artificial Sequence
<220> FEATURE:
<223> OTHER INFORMATION: Cloning Vector

<400> SEQUENCE: 15
cgtcgcggaa gggtatgagt aaacttggtc tga                         33

<210> SEQ ID NO 16
<211> LENGTH: 34
<212> TYPE: DNA
<213> ORGANISM: Artificial Sequence
<220> FEATURE:
<223> OTHER INFORMATION: Cloning Vector

<400> SEQUENCE: 16
tccgcgaagg gtatacttta gattgattta aaac                        34

<210> SEQ ID NO 17
<211> LENGTH: 33
<212> TYPE: DNA
<213> ORGANISM: Artificial Sequence
<220> FEATURE:
<223> OTHER INFORMATION: Cloning Vector

<400> SEQUENCE: 17
tatacgcgcc ccccgcgcgc cccccgcgcg tat                         33

<210> SEQ ID NO 18
<211> LENGTH: 33
<212> TYPE: DNA
<213> ORGANISM: Artificial Sequence
<220> FEATURE:
<223> OTHER INFORMATION: Cloning Vector

<400> SEQUENCE: 18
atatgcgcgg ggggcgcgcg gggggcgcgc ata                         33

<210> SEQ ID NO 19
<211> LENGTH: 22
<212> TYPE: DNA
<213> ORGANISM: Artificial Sequence
<220> FEATURE:
<223> OTHER INFORMATION: Cloning Vector

<400> SEQUENCE: 19
cgcgcccccc gcgcgtatta ta                                     22

<210> SEQ ID NO 20
<211> LENGTH: 22
<212> TYPE: DNA
<213> ORGANISM: Artificial Sequence

```
<220> FEATURE:
<223> OTHER INFORMATION: Cloning Vector

<400> SEQUENCE: 20
ataatatgcg cgggggcgc gc                                          22

<210> SEQ ID NO 21
<211> LENGTH: 19
<212> TYPE: DNA
<213> ORGANISM: Artificial Sequence
<220> FEATURE:
<223> OTHER INFORMATION: Cloning Vector

<400> SEQUENCE: 21
cccttggcag tgggaaggg                                             19

<210> SEQ ID NO 22
<211> LENGTH: 19
<212> TYPE: DNA
<213> ORGANISM: Artificial Sequence
<220> FEATURE:
<223> OTHER INFORMATION: Cloning Vector

<400> SEQUENCE: 22
gggaaccgtc acccttccc                                             19

<210> SEQ ID NO 23
<211> LENGTH: 31
<212> TYPE: DNA
<213> ORGANISM: Artificial Sequence
<220> FEATURE:
<223> OTHER INFORMATION: Cloning Vector

<400> SEQUENCE: 23
cgcgcccccg cgcgtatccc ttggcagtgg g                               31

<210> SEQ ID NO 24
<211> LENGTH: 8
<212> TYPE: DNA
<213> ORGANISM: Artificial Sequence
<220> FEATURE:
<223> OTHER INFORMATION: Cloning Vector

<400> SEQUENCE: 24 atagggaa                                                          8

<210> SEQ ID NO 25
<211> LENGTH: 9
<212> TYPE: DNA
<213> ORGANISM: Artificial Sequence
<220> FEATURE:
<223> OTHER INFORMATION: Cloning Vector

<400> SEQUENCE: 25 aagggtata                                                         9

<210> SEQ ID NO 26
<211> LENGTH: 32
<212> TYPE: DNA
<213> ORGANISM: Artificial Sequence
<220> FEATURE:
<223> OTHER INFORMATION: Cloning Vector

<400> SEQUENCE: 26
ccgtcaccct tcccatatgc gcgggggcgc gc                              32
```

<210> SEQ ID NO 27
<211> LENGTH: 31
<212> TYPE: DNA
<213> ORGANISM: Artificial Sequence
<220> FEATURE:
<223> OTHER INFORMATION: Cloning Vector

<400> SEQUENCE: 27
aagggtatac gcgcccccgc gcgtatccct t                            31

<210> SEQ ID NO 28
<211> LENGTH: 31
<212> TYPE: DNA
<213> ORGANISM: Artificial Sequence
<220> FEATURE:
<223> OTHER INFORMATION: Cloning Vector

<400> SEQUENCE: 28
ttcccatatg cgcggggcg cgcataggga a                             31

<210> SEQ ID NO 29
<211> LENGTH: 32
<212> TYPE: DNA
<213> ORGANISM: Artificial Sequence
<220> FEATURE:
<223> OTHER INFORMATION: Cloning Vector

<400> SEQUENCE: 29
atcactagtt tttttttttt tttttttttt tt                           32

<210> SEQ ID NO 30
<211> LENGTH: 8
<212> TYPE: DNA
<213> ORGANISM: Artificial Sequence
<220> FEATURE:
<223> OTHER INFORMATION: Cloning Vector

<400> SEQUENCE: 30 tagtgatc                                                      8

<210> SEQ ID NO 31
<211> LENGTH: 12
<212> TYPE: DNA
<213> ORGANISM: Artificial Sequence
<220> FEATURE:
<223> OTHER INFORMATION: Cloning Vector

<400> SEQUENCE: 31
aagggcgtct tc                                                 12

<210> SEQ ID NO 32
<211> LENGTH: 12
<212> TYPE: DNA
<213> ORGANISM: Artificial Sequence
<220> FEATURE:
<223> OTHER INFORMATION: Cloning Vector

<400> SEQUENCE: 32
ttcccgcaga ag                                                 12

<210> SEQ ID NO 33
<211> LENGTH: 13
<212> TYPE: DNA
<213> ORGANISM: Artificial Sequence
<220> FEATURE:
<223> OTHER INFORMATION: Cloning Vector

<400> SEQUENCE: 33
aagggcgtct tcc                                                          13

<210> SEQ ID NO 34
<211> LENGTH: 13
<212> TYPE: DNA
<213> ORGANISM: Artificial Sequence
<220> FEATURE:
<223> OTHER INFORMATION: Cloning Vector

<400> SEQUENCE: 34
cgcagaaggc cgg                                                          13

<210> SEQ ID NO 35
<211> LENGTH: 53
<212> TYPE: DNA
<213> ORGANISM: Artificial Sequence
<220> FEATURE:
<223> OTHER INFORMATION: Cloning Vector

<400> SEQUENCE: 35
gtgccgagcg tgcgaagggc gtcttccggc cttttttttt tttttttttt ttt              53

<210> SEQ ID NO 36
<211> LENGTH: 31
<212> TYPE: DNA
<213> ORGANISM: Artificial Sequence
<220> FEATURE:
<223> OTHER INFORMATION: Cloning Vector

<400> SEQUENCE: 36
cacggctcgc acgcttcccg cagaaggccg g                                      31

<210> SEQ ID NO 37
<211> LENGTH: 40
<212> TYPE: DNA
<213> ORGANISM: Artificial Sequence
<220> FEATURE:
<223> OTHER INFORMATION: Cloning Vector

<400> SEQUENCE: 37
aagggcgtct tcggcctttt tttttttttt tttttttttt                             40

<210> SEQ ID NO 38
<211> LENGTH: 16
<212> TYPE: DNA
<213> ORGANISM: Artificial Sequence
<220> FEATURE:
<223> OTHER INFORMATION: Cloning Vector

<400> SEQUENCE: 38
ttcccgcaga agccgg                                                       16

<210> SEQ ID NO 39
<211> LENGTH: 24
<212> TYPE: DNA
<213> ORGANISM: Artificial Sequence
<220> FEATURE:
<223> OTHER INFORMATION: Cloning Vector

<400> SEQUENCE: 39
cccttcgcgg acgtcgcgga aggg                                              24

<210> SEQ ID NO 40

-continued

```
<211> LENGTH: 24
<212> TYPE: DNA
<213> ORGANISM: Artificial Sequence
<220> FEATURE:
<223> OTHER INFORMATION: Cloning Vector

<400> SEQUENCE: 40
gggaagcgcc tgcagcgcct tccc                                             24

<210> SEQ ID NO 41
<211> LENGTH: 24
<212> TYPE: DNA
<213> ORGANISM: Artificial Sequence
<220> FEATURE:
<223> OTHER INFORMATION: Cloning Vector

<400> SEQUENCE: 41
cgcggaaggg cccttggcag tggg                                             24

<210> SEQ ID NO 42
<211> LENGTH: 19
<212> TYPE: DNA
<213> ORGANISM: Artificial Sequence
<220> FEATURE:
<223> OTHER INFORMATION: Cloning Vector

<400> SEQUENCE: 42
tgcagcgcct tcccgggaa                                                   19

<210> SEQ ID NO 43
<211> LENGTH: 19
<212> TYPE: DNA
<213> ORGANISM: Artificial Sequence
<220> FEATURE:
<223> OTHER INFORMATION: Cloning Vector

<400> SEQUENCE: 43
aagggccctt cgcggacgt                                                   19

<210> SEQ ID NO 44
<211> LENGTH: 24
<212> TYPE: DNA
<213> ORGANISM: Artificial Sequence
<220> FEATURE:
<223> OTHER INFORMATION: Cloning Vector

<400> SEQUENCE: 44
ccgtcaccct tcccgggaag cgcc                                             24

<210> SEQ ID NO 45
<211> LENGTH: 15
<212> TYPE: DNA
<213> ORGANISM: Artificial Sequence
<220> FEATURE:
<223> OTHER INFORMATION: Cloning Vector

<400> SEQUENCE: 45
cgcggaaggg ccctt                                                       15

<210> SEQ ID NO 46
<211> LENGTH: 10
<212> TYPE: DNA
<213> ORGANISM: Artificial Sequence
<220> FEATURE:
<223> OTHER INFORMATION: Cloning Vector

<400> SEQUENCE: 46
```

```
ttcccgggaa                                                             10

<210> SEQ ID NO 47
<211> LENGTH: 10
<212> TYPE: DNA
<213> ORGANISM: Artificial Sequence
<220> FEATURE:
<223> OTHER INFORMATION: Cloning Vector

<400> SEQUENCE: 47
aagggccctt                                                             10

<210> SEQ ID NO 48
<211> LENGTH: 15
<212> TYPE: DNA
<213> ORGANISM: Artificial Sequence
<220> FEATURE:
<223> OTHER INFORMATION: Cloning Vector

<400> SEQUENCE: 48
ttcccgggaa gcgcc                                                       15

<210> SEQ ID NO 49
<211> LENGTH: 10
<212> TYPE: DNA
<213> ORGANISM: Artificial Sequence
<220> FEATURE:
<223> OTHER INFORMATION: Cloning Vector

<400> SEQUENCE: 49
aagggccctt                                                             10

<210> SEQ ID NO 50
<211> LENGTH: 10
<212> TYPE: DNA
<213> ORGANISM: Artificial Sequence
<220> FEATURE:
<223> OTHER INFORMATION: Cloning Vector

<400> SEQUENCE: 50
ttcccgggaa                                                             10
```